United States Patent
Stevenson

(10) Patent No.: US 7,489,495 B2
(45) Date of Patent: Feb. 10, 2009

(54) APPARATUS AND PROCESS FOR REDUCING THE SUSCEPTIBILITY OF ACTIVE IMPLANTABLE MEDICAL DEVICES TO MEDICAL PROCEDURES SUCH AS MAGNETIC RESONANCE IMAGING

(75) Inventor: Robert A. Stevenson, Canyon Country, CA (US)

(73) Assignee: Greatbatch-Sierra, Inc., Clarence, NY (US)

(*) Notice: Subject to any disclaimer, the term of this patent is extended or adjusted under 35 U.S.C. 154(b) by 639 days.

(21) Appl. No.: 11/163,845

(22) Filed: Nov. 1, 2005

(65) Prior Publication Data

US 2006/0085043 A1     Apr. 20, 2006

Related U.S. Application Data

(63) Continuation-in-part of application No. 11/097,999, filed on Mar. 31, 2005, which is a continuation-in-part of application No. 10/825,900, filed on Apr. 15, 2004, now Pat. No. 6,999,818, application No. 11/163,845, which is a continuation-in-part of application No. 11/161,730, filed on Aug. 15, 2005, now Pat. No. 7,035,076.

(60) Provisional application No. 60/724,479, filed on Oct. 6, 2005.

(51) Int. Cl.
*H01G 4/35* (2006.01)
*H01G 4/236* (2006.01)
*H01G 4/228* (2006.01)

(52) U.S. Cl. ............ 361/302; 361/307; 361/306.2; 607/5

(58) Field of Classification Search .......... 361/302, 361/306.1–306.3, 307, 308.1–308.3, 309–311, 361/301.2; 607/5; 333/182–185
See application file for complete search history.

(56) References Cited

U.S. PATENT DOCUMENTS

| | | | |
|---|---|---|---|
| 4,424,551 A | 1/1984 | Stevenson et al. | |
| 5,217,010 A | 6/1993 | Tsitlik et al. | |
| 5,333,095 A | 7/1994 | Stevenson et al. | |
| 5,751,539 A | 5/1998 | Stevenson et al. | |
| 5,905,627 A | 5/1999 | Brendel et al. | |
| 5,973,906 A | 10/1999 | Stevenson et al. | |
| 6,008,980 A | 12/1999 | Stevenson et al. | |
| 6,529,103 B1 | 3/2003 | Brendel et al. | |
| 6,566,978 B2 | 5/2003 | Stevenson et al. | |
| 6,765,144 B1 | 7/2004 | Wang et al. | |
| 6,765,779 B2 | 7/2004 | Stevenson et al. | |
| 6,765,780 B2 | 7/2004 | Brendel et al. | |
| 6,815,609 B1 | 11/2004 | Wang et al. | |
| 2005/0197677 A1 | 9/2005 | Stevenson | |

*Primary Examiner*—Carl H Layno
*Assistant Examiner*—Yun Haeng Lee
(74) *Attorney, Agent, or Firm*—Kelly Lowry & Kelley LLP

(57) ABSTRACT

A feedthrough terminal assembly for an active implantable medical device (AIMD) includes magnetic shielding elements to block incident magnetic fields during medical procedures such as Magnetic Resonance Imaging. The assembly includes conductive or ground plate(s) embedded in an insulator surrounding elements of the assembly, a plurality of lead wires extending from electronic circuitry of the AIMD, and a lossy ferrite inductor through which the lead wires extend in non-conductive relation for increasing the impedance of the lead wires at selected RF frequencies. Alternatively, the assembly includes a conductive sleeve or cap surrounding the feedthrough capacitor and/or conductive support.

52 Claims, 12 Drawing Sheets

BODY FLUID SIDE

APPARATUS AND PROCESS FOR REDUCING THE SUSCEPTIBILITY OF ACTIVE IMPLANTABLE MEDICAL DEVICES TO MEDICAL PROCEDURES SUCH AS MAGNETIC RESONANCE IMAGING

BACKGROUND OF THE INVENTION

This invention relates generally to EMI filter assemblies, particularly of the type used in active implantable medical devices (AIMDs) such as cardiac pacemakers, cardioverter defibrillators, neurostimulators and the like, which decouple and shield internal electronic components of the medical device from undesirable electromagnetic interference (EMI) signals.

Compatibility of cardiac pacemakers, implantable defibrillators and other types of active implantable medical devices with magnetic resonance imaging (MRI) and other types of hospital diagnostic equipment has become a major issue. If one goes to the websites of the major cardiac pacemaker manufacturers in the United States, which include St. Jude Medical, Medtronic and Guidant, one will see that the use of MRI is generally contra-indicated with pacemakers and implantable defibrillators. See also "Safety Aspects of Cardiac Pacemakers in Magnetic Resonance Imaging", a dissertation submitted to the Swiss Federal Institute of Technology Zurich presented by Roger Christoph Luchinger. "Dielectric Properties of Biological Tissues: I. Literature Survey", by C. Gabriel, S. Gabriel and E. Cortout; "Dielectric Properties of Biological Tissues: II. Measurements and the Frequency Range 0 Hz to 20 GHz", by S. Gabriel, R. W. Lau and C. Gabriel; "Dielectric Properties of Biological Tissues: III. Parametric Models for the Dielectric Spectrum of Tissues", by S. Gabriel, R. W. Lau and C. Gabriel; and "Advanced Engineering Electromagnetics, C. A. Balanis, Wiley, 1989, all of which are incorporated herein by reference.

However, an extensive review of the literature indicates that MRI is indeed often used with pacemaker patients. The safety and feasibility of MRI in patients with cardiac pacemakers is an issue of gaining significance. The effects of MRI on patients' pacemaker systems have only been analyzed retrospectively in some case reports. There are a number of papers that indicate that MRI on new generation pacemakers can be conducted up to 0.5 Tesla (T). MRI is one of medicine's most valuable diagnostic tools. An absolute contra-indication for pacemaker patients means that pacemaker and ICD wearers are excluded from MRI. This is particularly true of scans of the thorax and abdominal areas. Because of MRI's incredible value as a diagnostic tool for imaging organs and other body tissues, many physicians simply take the risk and go ahead and perform MRI on a pacemaker patient. The literature indicates a number of precautions that physicians should take in this case, including limiting the power of the MRI magnetic field, programming the pacemaker to fixed or asynchronous pacing mode, and then careful reprogramming and evaluation of the pacemaker and patient after the procedure is complete. There have been reports of latent problems with cardiac pacemakers after an MRI procedure occurring many days later.

There are three types of electromagnetic fields used in an MRI unit. The first type is the main static magnetic field which is used to align protons in body tissue. The field strength varies from 0.5 to 3.0 Tesla in most of the currently available MRI units in clinical use. Some of the newer MRI system fields can go as high as 4 to 5 Tesla. This is about 100,000 times the magnetic field strength of the earth. A static magnetic field can induce powerful mechanical forces on any magnetic materials implanted within the patient. This would include certain components within the cardiac pacemaker itself and/or lead wire systems. It is not likely (other than sudden system shut down) that the static MRI magnetic field can induce currents into the pacemaker lead wire system and hence into the pacemaker itself. It is a basic principle of physics that a magnetic field must either be time-varying as it cuts across the conductor, or the conductor itself must move within the magnetic field for currents to be induced.

The second type of field produced by magnetic resonance imaging is the pulsed RF field which is generated by the body coil or head coil. This is used to change the energy state of the protons and illicit MRI signals from tissue. The RF field is homogeneous in the central region and has two main components: (1) the magnetic field is circularly polarized in the actual plane; and (2) the electric field is related to the magnetic field by Maxwell's equations. In general, the RF field is switched on and off during measurements and usually has a frequency of 21 MHz to 64 MHz to 128 MHz depending upon the static magnetic field strength.

The third type of electromagnetic field is the time-varying magnetic gradient fields which are used for spatial localization. These change their strength along different orientations and operating frequencies on the order of 1 kHz. The vectors of the magnetic field gradients in the X, Y and Z directions are produced by three sets of orthogonally positioned coils and are switched on only during the measurements.

Feedthrough terminal pin assemblies are generally well known in the art for use in connecting electrical signals through the housing or case of an electronic instrument. For example, in implantable medical devices such as cardiac pacemakers, defibrillators and the like, the terminal pin assembly comprises one or more conductive terminal pins supported by an insulator structure for feedthrough passage of electrical signals from the exterior to the interior of the medical device. Many different insulator structures and related mounting methods are known for use in medical devices wherein the insulator structure provides a hermetic seal to prevent entry of patient body fluids into the medical device housing, where such body fluids could otherwise interfere with the operation of and/or cause damage to internal electronic components of the medical device.

In the past, two primary technologies have been employed to manufacture the hermetic seal. One technique involves the use of an alumina insulator which is metallized to accept brazing material. This alumina insulator is brazed to the terminal pin or pins, and also to an outer metal ferrule of titanium or the like. The alumina insulator supports the terminal pin or pins in insulated spaced relation from the ferrule which is adapted for suitable mounting within an access opening formed in the housing of the medical device. In an alternative technique, the hermetic seal comprises a glass-based seal forming a compression or matched fused glass seal for supporting the terminal pin or pins within an outer metal ferrule or housing.

The feedthrough terminal pins are typically connected to one or more lead wires which, in the example of a cardiac pacemaker, sense signals from the patient's heart and also couple electronic pacing pulses from the medical device to the patient's heart. Unfortunately, these lead wires can act as an antenna to collect stray electromagnetic interference (EMI) signals for transmission via the terminal pins into the interior of the medical device. Such unwanted EMI signals can disrupt proper operation of the medical device, resulting in malfunction or failure. For example, it has been documented that stray EMI signals emanating from cellular telephones can inhibit pacemaker operation, resulting in asynchronous pacing, tracking and missed beats. To address this problem, hermetically sealed feedthrough terminal pin assemblies have been designed to include a feedthrough capacitor for decoupling EMI signals in a manner preventing such unwanted signals from entering the housing of the implantable medical device. See, for example, U.S. Pat. Nos. 4,424,551; 5,333,095; 5,751,539; 5,905,627; 5,973,906; 6,008,980; and 6,566.978. These prior art feedthrough capacitor EMI filters generally provide a high degree of attenuation to EMI in the frequency range between 450 and 3000 MHz.

While feedthrough capacitor filter assemblies have provided a significant advance in the art, a remaining area of concern is powerful lower frequency emitters like MRI. As previously mentioned, feedthrough capacitors, as described in the prior art, work by providing a low impedance to ground (to the overall electromagnetic shield of the implantable medical device) thereby by-passing such high frequency signals before they can enter and disrupt sensitive pacemaker electronic circuitry. However, when a pacemaker lead wire system is exposed to a powerful time varying electromagnetic field, such as induced by MRI, the last thing that is desirable is to create low impedance in the lead wire system. A low impedance in the lead wire system only increases the current that would flow in the lead wires thereby creating additional lead wire heating and/or myocardial tissue necrosis at the pacemaker TIP to RING interface. Accordingly, it would be desirable to actually raise the impedance of the lead wire system at certain critical frequencies thereby reducing the undesirable currents in the lead wire system.

It is instructive to note how voltages and EMI are induced into an implanted lead wire system. At very low frequency (VLF), voltages are induced at the input to the cardiac pacemaker as currents circulate throughout the patient's body. Because of the vector displacement between the pacemaker housing and, for example, the TIP electrode, voltage drop across body tissues may be sensed due to Ohms Law and the circulating RF signal. At higher frequencies, the implanted lead wire systems actually act as antennas where currents are induced along their length. These antennas are not very efficient due to the damping effects of body tissue; however, this can often be offset by body resonances. At very high frequencies (such as cellular telephone frequencies), EMI signals are induced only into the first area of the lead wire system (for example, at the header block of a cardiac pacemaker). This has to do with the wavelength of the signals involved and where they couple efficiently into the system.

Magnetic field coupling into an implanted lead wire system is based on loop areas. For example, in a cardiac pacemaker, there is a loop formed by the lead wire as it comes from the cardiac pacemaker housing to its distal TIP located in the right ventricle. The return path is through body fluid and tissue generally straight from the TIP electrode in the right ventricle back up to the pacemaker case or housing. This forms an enclosed area which can be measured from patient X-rays in square centimeters. The average loop area is 200 to 225 square centimeters. This is an average and is subject to great statistical variation. For example, in a large adult patient with an abdominal implant, the implanted loop area is much larger (greater than 450 square centimeters).

Relating now to the specific case of MRI, the magnetic gradient fields would be induced through enclosed loop areas. However, the pulsed RF fields, which are generated by the body coil, would be primarily induced into the lead wire system by antenna action.

There are a number of potential problems with MRI, including:

(1) Closure of the pacemaker reed switch. A pacemaker reed switch, which can also be a Hall Effect device, is designed to detect a permanent magnet held close to the patient's chest. This magnet placement allows a physician or even the patient to put the implantable medical device into what is known as the magnet mode response. The magnet mode response varies from one manufacturer to another, however, in general, this puts the pacemaker into a fixed rate or asynchronous pacing mode. This is normally done for short times and is very useful for diagnostic purposes. However, when a pacemaker is brought close to the MRI scanner, the MRI static field can make the pacemaker's internal reed switch close, which puts the pacemaker into a fixed rate or asynchronous pacing mode. Worse yet, the reed switch may bounce or oscillate. Asynchronous pacing may compete with the patient's underlying cardiac rhythm. This is one reason why patients have generally been advised not to undergo MRI. Fixed rate or asynchronous pacing for most patients is not an issue. However, in patients with unstable conditions, such as myocardial ischemia, there is a substantial risk for ventricular fibrillation during asynchronous pacing. In most modern pacemakers the magnetic reed switch (or Hall Effect device) function is programmable. If the magnetic reed switch response is switched off, then synchronous pacing is still possible even in strong magnetic fields. The possibility to open and re-close the reed switch in the main magnetic field by the gradient field cannot be excluded. However, it is generally felt that the reed switch will remain closed due to the powerful static magnetic field. It is theoretically possible for certain reed switch orientations at the gradient field to be capable of repeatedly closing and re-opening the reed switch.

(2) Reed switch damage. Direct damage to the reed switch is theoretically possible, but has not been reported in any of the known literature. In an article written by Roger Christoph Luchinger of Zurich, he reports on testing in which reed switches were exposed to the static magnetic field of MRI equipment. After extended exposure to these static magnetic fields, the reed switches functioned normally at close to the same field strength as before the test.

(3) Pacemaker displacement. Some parts of pacemakers, such as the batteries and reed switch, contain ferrous magnetic materials and are thus subject to mechanical forces during MRI. Pacemaker displacement may occur in response to magnetic force or magnetic torque.

(4) Radio frequency field. At the frequencies of interest in MRI, RF energy can be absorbed and converted to heat. The power deposited by RF pulses during MRI is complex and is dependent upon the power and duration of the RF pulse, the transmitted frequency, the number of RF pulses applied per unit time, and the type of configuration of the RF transmitter coil used. The amount of heating also depends upon the volume of tissue imaged, the electrical resistivity of tissue and the configuration of the anatomical region imaged. Other variables that affect the degree of heating depend on the placement in the human body of the AIMD and its associated lead wire(s). For example, it will make a difference how much current is induced into a pacemaker lead wire system as to whether it is a left or right pectoral implant. In addition, the routing of the lead and the lead length are also very critical as to the amount of induced current and heating that would occur. Also, distal Tip design is very important as the distal Tip itself can act as its own antenna. The cause of heating in an MRI environment is two fold: (a) RF field coupling to the lead can occur which induces significant local heating; and (b) currents induced during the RF transmission can cause local Ohms Law heating next to the distal TIP electrode of the implanted lead. The RF field in an MRI scanner can produce enough energy to induce lead wire currents sufficient to destroy some of the adjacent myocardial tissue. Ablation has also been observed. The effects of this heating are not readily detectable by monitoring during the MRI. Indications that heating has occurred would include an increase in pacing threshold, myocardial perforation and lead penetration, or even arrhythmias caused by scar tissue. Such long term heating effects of MRI have not been well studied yet.

(5) Alterations of pacing rate due to the applied radio frequency field. It has been observed that the RF field may induce undesirable fast pacing (QRS complex) rates. There are various mechanisms which have been proposed to explain rapid pacing: direct tissue stimulation, interference with pacemaker electronics or pacemaker reprogramming (or reset). In all of these cases, it would be desirable to raise the impedance, make the feedthrough capacitor more effective and provide a very high degree of protection to AIMD electronics. This will make alterations in pacemaker pacing rate and/or pacemaker reprogramming much more unlikely.

(6) Time-varying magnetic gradient fields. The contribution of the time-varying gradient to the total strength of the MRI magnetic field is negligible, however, pacemaker systems could be affected because these fields are rapidly applied and removed. The time rate of change of the magnetic field is directly related to how much electromagnetic force and hence current can be induced into a lead wire system. Luchinger reports that even using today's gradient systems with a time-varying field up to 50 Tesla per second, the induced currents are likely to stay below the biological thresholds for cardiac fibrillation. A theoretical upper limit for the induced voltage by the time-varying magnetic gradient field is 20 volts. Such a voltage during more than 0.1 milliseconds could be enough energy to directly pace the heart.

(7) Heating. Currents induced by time-varying magnetic gradient fields may lead to local heating. Researchers feel that the calculated heating effect of the gradient field is much less as compared to that caused by the RF field and therefore may be neglected.

There are additional problems possible with implantable cardioverter defibrillators (ICDs). ICDs use different and larger batteries which could cause higher magnetic forces. The programmable sensitivity in ICDs is normally much higher than it is for pacemakers, therefore, ICDs may falsely detect a ventricular tachyarrhythmia and inappropriately deliver therapy. In this case, therapy might include anti-tachycardia pacing, cardio version or defibrillation (high voltage shock) therapies. MRI magnetic fields may prevent detection of a dangerous ventricular arrhythmia or fibrillation. There can also be heating problems of ICD leads which are expected to be comparable to those of pacemaker leads. Ablation of vascular walls is another concern. Fortunately, ICDs have a sort of built-in fail-safe mechanism. That is, if during an MRI procedure, they inadvertently sense the MRI fields as a dangerous ventricular arrhythmia, the ICD will attempt to charge up and deliver a high voltage shock. However, there is a transformer contained within the ICD that is necessary to function in order to charge up the high energy storage capacitor contained within the ICD. In the presence of the main static field of the MRI the core of this transformer tends to saturate thereby preventing the high voltage capacitor from charging up. This makes it highly unlikely that a ICD patient undergoing an MRI would receive an inappropriate high voltage shock therapy.

In summary, there are a number of studies that have shown that MRI patients with active implantable medical devices, such as cardiac pacemakers, can be at risk for potential hazardous effects. However, there are a number of anecdotal reports that MRI can be safe for extremity imaging of pacemaker patients (only when an MRI is thought to be an absolute diagnostic necessity). The effect of an MRI system on the function of pacemakers, ICDs and neurostimulators depends on various factors, including the strength of the static magnetic field, the pulse sequence (gradient and RF field used), the anatomic region being imaged, and many other factors. Further complicating this is the fact that each manufacturer's pacemaker and ICD designs behave differently. Most experts still conclude that MRI for the pacemaker patient should not be considered safe. Paradoxically, this also does not mean that the patient should not receive MRI. The physician must make an evaluation given the pacemaker patient's condition and weigh the potential risks of MRI against the benefits of this powerful diagnostic tool. As MRI technology progresses, including higher field gradient changes over time applied to thinner tissue slices at more rapid imagery, the situation will continue to evolve and become more complex. An example of this paradox is a pacemaker patient who is suspected to have a cancer of the lung. Treatment of such a tumor may require stereotactic imaging only made possible through fine focus MRI. With the patient's life literally at risk, the physician may make the decision to perform MRI in spite of all of the previously described attendant risks to the pacemaker system.

It is clear that MRI will continue to be used in patients with an implantable medical device. There are a number of other hospital procedures, including electrocautery surgery, lithotripsy, etc., to which a pacemaker patient may also be exposed. Accordingly, there is a need for circuit protection devices which will improve the immunity of active implantable medical device systems to diagnostic procedures such as MRI. There is also a need to provide increased filtering for AIMD's due to the recent proliferation in the marketplace of new higher power emitters. These include aftermarket cellular telephone amplifiers, associated higher gain antennas and radio frequency identification (RFID) readers and scanners. The present invention fulfills all of these needs and provides other related advantages.

SUMMARY OF THE INVENTION

The present invention resides in a feedthrough terminal assembly for an active implantable medical device (AIMD) having magnetic shielding characteristics, comprising a ferrule defining a central aperture, an insulator disposed over the central aperture of the ferrule having a conductive plate embedded in the insulator forming an interior magnetic shield across substantially the entire central aperture of the ferrule. In the preferred embodiment, this assembly includes a feedthrough capacitor disposed on an axial side of the insulator, the feedthrough capacitor having first and second sets of electrode plates, the second set of electrode plates being conductively coupled to the ferrule or a housing or a ground plane. One or more lead wires extend through the insulator and the feedthrough capacitor in non-conductive relation with the ferrule and conductively coupled to the first set of electrode plates.

The interior magnetic shield may be a single conductive plate or a set of conductive plates embedded in the insulator. The conductive plate(s) are comprised of thin materials that contain magnetic dipoles, such as nickel, ferrous metals, and certain nano-powders. The assembly may also include an exterior magnetic shield peripherally surrounding at least a portion of the ferrule and/or feedthrough capacitor and/or its associated inductor slab(s). It should be noted that the exterior magnetic shield assembly can be used with or without the previously described embedded magnetic shield plates within the insulator. The exterior magnetic shield may comprise a conductive sleeve or cap disposed over the feedthrough capacitor and/or its associated inductor or lossy inductor slab opposite the insulator. The exterior magnetic shield may also comprise a conductive plate disposed between the insulator and the feedthrough capacitor through which the lead wires pass in non-conductive relation. As with the interior magnetic shield, the exterior magnetic shield may be comprised of a ferro-magnetic material such as nickel or nickel alloy.

The assembly may further include a lossy ferrite inductor disposed between the capacitor and the insulator through which the lead wires extend in non-conductive relation. When a lossy ferrite inductor is present, the assembly may comprise one or more feedthrough capacitors associated with the inductor disposed adjacent to opposite surfaces of the inductor. With multiple capacitors, the first set of electrode plates are conductively coupled to the lead wire and the second set of electrode plates are conductively coupled to the housing ferrule or ground plane.

The assembly is suitable for use in an active implantable medical device including a cardiac pacemaker, an implantable defibrillator, a congestive heart failure device, a hearing implant, a cochlear implant, a neurostimulator, a drug pump, a ventricular assist device, an insulin pump, a spinal cord stimulator, an implantable sensing system, a deep brain stimulator, an artificial heart, an incontinence device, a vagus nerve stimulator, a bone growth stimulator, a bion, a gastric pacemaker, or a prosthetic device.

Other features and advantages of the present invention will become apparent from the following more detailed description, taken in conjunction with the accompanying drawings which, by way of example, illustrate the principles of the invention.

BRIEF DESCRIPTION OF THE DRAWINGS

The accompanying drawings illustrate the invention. In such drawings.

DETAILED DESCRIPTION OF THE PREFERRED EMBODIMENTS

Figure 1:
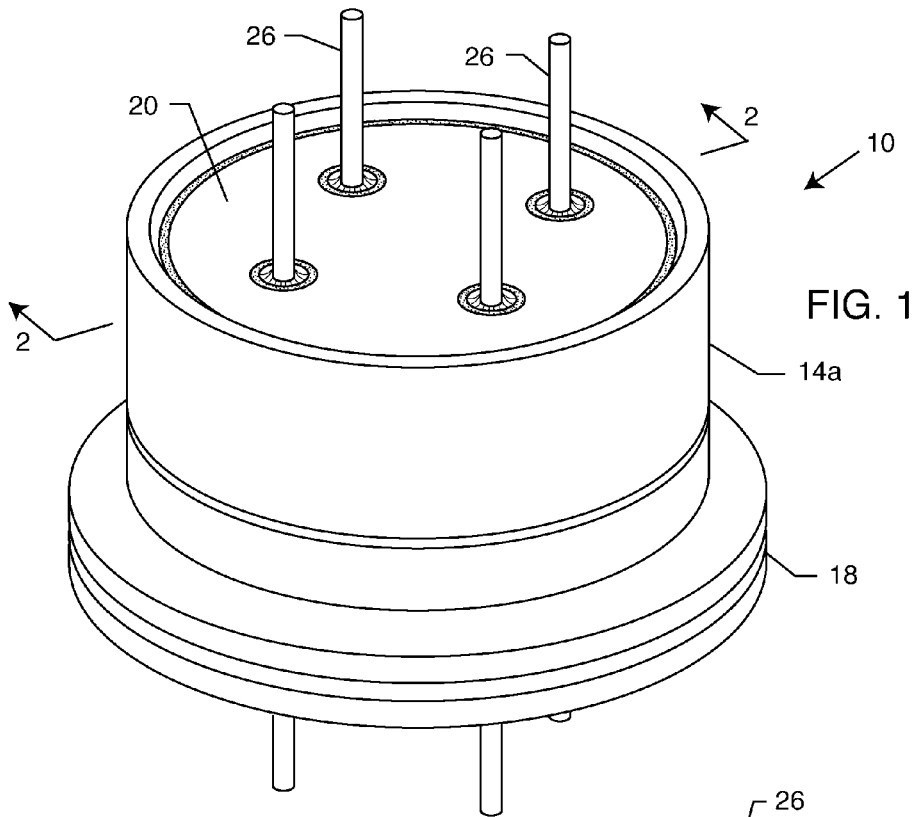
FIG. 1 is a perspective view of a quadpolar $L_2$ filter feedthrough terminal assembly incorporating magnetic shield elements of the present invention.
Figure 2:
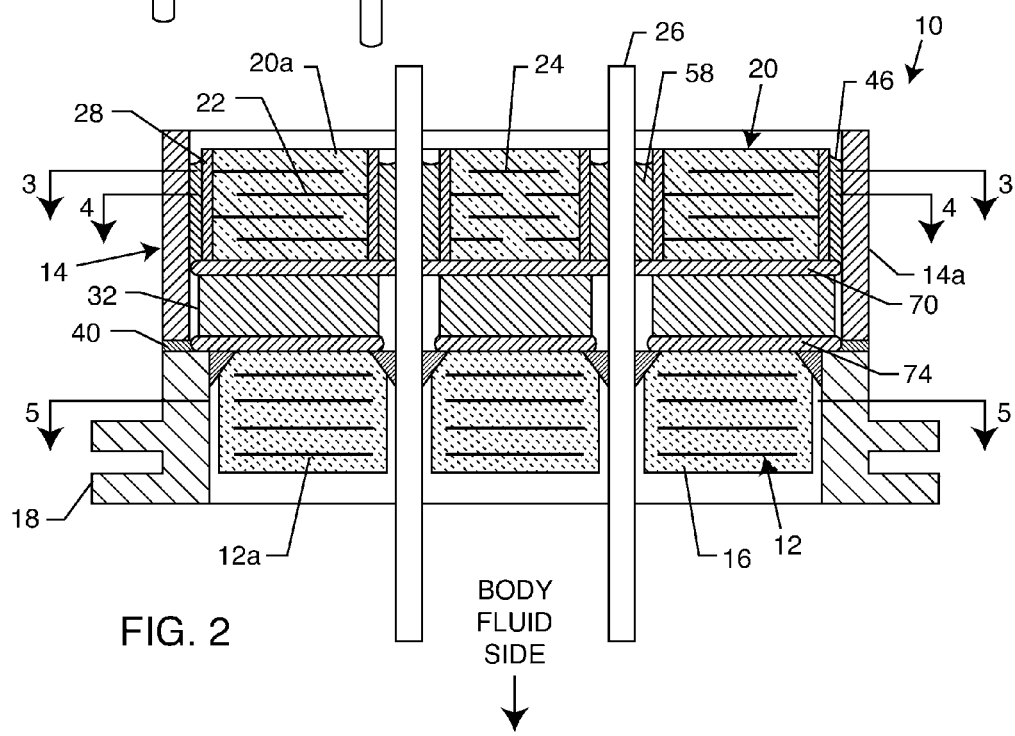
FIG. 2 is a cross-sectional view of the quadpolar feedthrough terminal assembly shown taken along line 2-2 in FIG. 1.

As shown in the drawings for purposes of illustration, the present invention relates to a feedthrough terminal assembly having magnetic shielding characteristics. FIGS. 1 and 2 illustrate a preferred embodiment wherein a feedthrough terminal assembly has an interior magnetic shield 12 and an exterior magnetic shield 14. The interior magnetic shield 12 comprises a plate 12a or a set of plates 12a embedded in an insulator 16 disposed over a central aperture of a conductive support 18 of the assembly 10. The conductive support 18 may comprise a ferrule or a housing. The embedded plate(s) 12a are comprised of a ferro-magnetic material such as nickel or the like. There are a number of other suitable materials for the plate set 12 or 12a. This can include any material containing magnetic dipoles, such as various nano-materials and other compositions. In general, the plate set has a mass density of at least 0.005 grams per cubic centimeter, a saturization magnetization of from about 1 to about 50,000 gauss, a coercive force of from about 0.005 to about 10,000 Orsteds, a relative magnetic permeability from about 0.5 to about 750,000 and can have average particle sizes varying over a wide range. This includes the entire range of nano-particles which would generally have a particle size of less than 200 nanometers. For the purposes as further described herein, when reference is made to nickel, it is understood that nickel is representative of any ferro-magnetic material as having the properties as described above.

Figure 8:
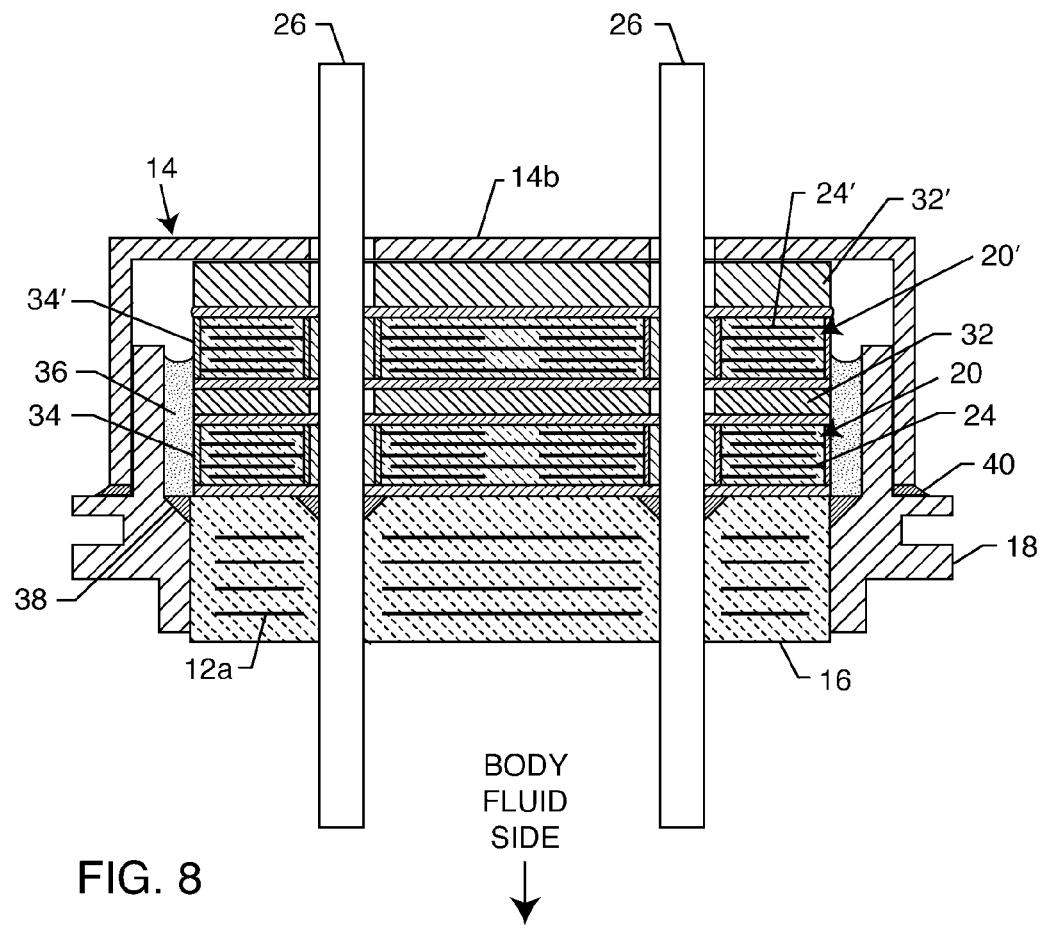
FIG. 8 is a cross-sectional view of a "LL" filtered feedthrough terminal quadpolar feedthrough terminal assembly incorporating magnetic shield elements of the present invention, wherein two inductors are stacked with two capacitors, wherein both capacitors are externally grounded, and wherein the ferrule of the hermetic terminal has been extended upwardly.
Figure 9:
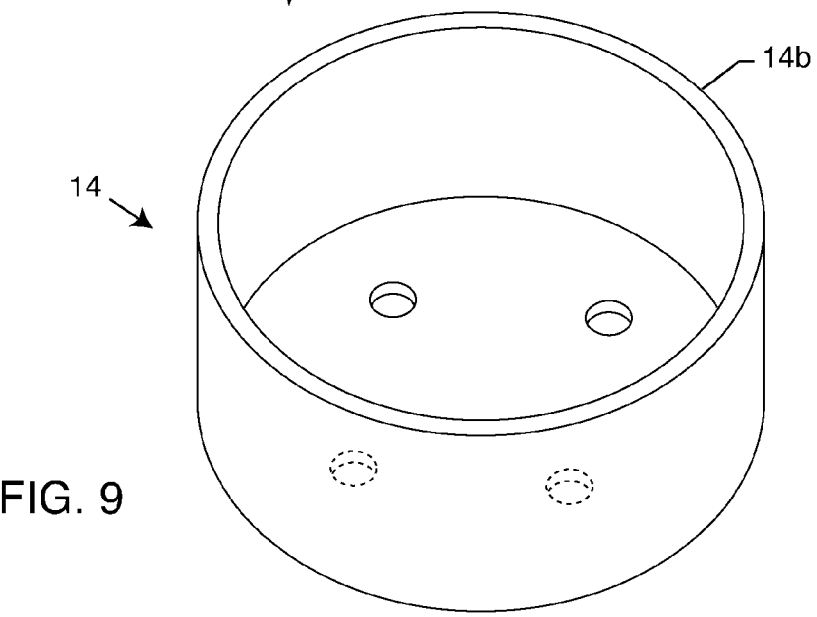
FIG. 9 is an illustration of the nickel enclosure shown in FIG. 8.

The exterior magnetic shield 14 comprises a sleeve 14a that peripherally surrounds at least a portion of the ferrule 18 and/or a feedthrough capacitor 20 on the assembly 10. The exterior magnetic shield 14 may be comprised of a ferro-magnetic material such as nickel, nickel alloy, or the like. The exterior magnetic shield 14 may also comprise a cap 14b which completely encloses the feedthrough capacitor opposite the insulator as shown in FIGS. 8 and 9. The conductive sleeve 14a makes contact to the gold braze area 40 to provide a reliable oxide-free electrical connection to the ferrule 18.

The capacitor 20 is disposed on an axial side of the insulator 16 and has first and second sets of electrode plates 22, 24 embedded within an insulative or dielectric body 20a. The second set of electrode plates 24 are conductively coupled via the exterior magnetic shield 14 to the ferrule 18 or a housing or ground plane associated with an active implantable medical device incorporating the feedthrough terminal assembly.

Figure 3:
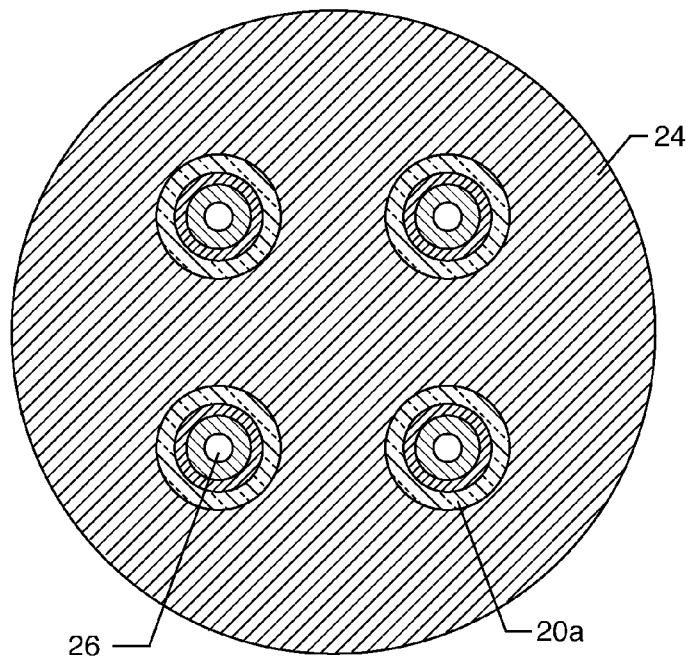
FIG. 3 is a cross-sectional view of the quadpolar feedthrough terminal assembly shown taken along line 3-3 in FIG. 2.
Figure 4:
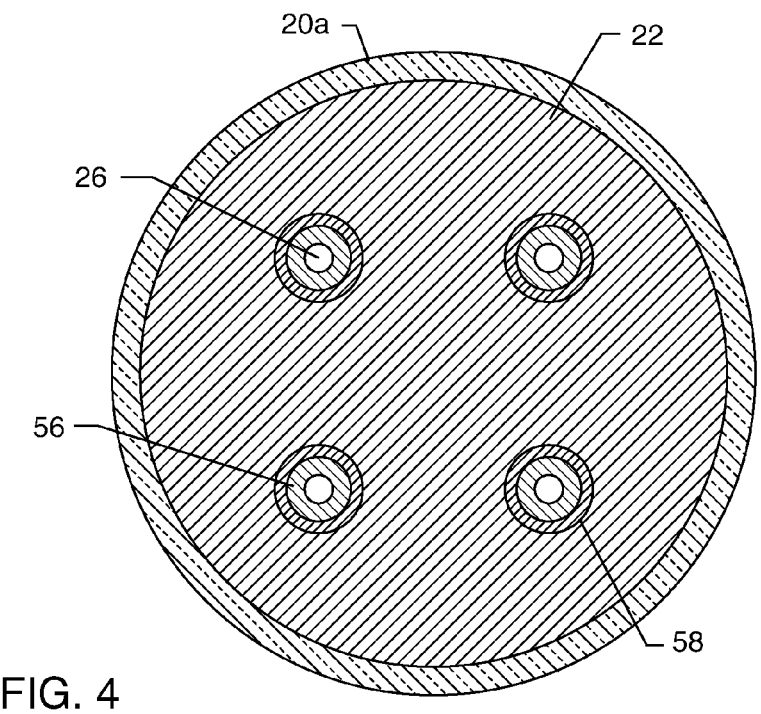
FIG. 4 is a cross-sectional view of the quadpolar feedthrough terminal assembly shown taken along line 4-4 in FIG. 2.

A lead wire 26 extends through the insulator 16 and the feedthrough capacitor 20 in non-conductive relation with the ferrule 18 and conductively coupled to the first set of electrode plates 22 in the capacitor 20. FIGS. 3 and 4 depict cross-sections of the feedthrough capacitor 20 shown in FIG. 2 and illustrate the first and second sets of electrode plates 22, 24. FIG. 3 shows the second set of electrode plates 24 in non-conductive relation with the lead wires 26 and extending to the outer edge of the feedthrough capacitor 20 to facilitate the conductive coupling with the ferrule 18, housing or ground plane. FIG. 4 illustrates the first set of electrode plates 22 that are conductively coupled to the lead wires 26.

Figure 5:
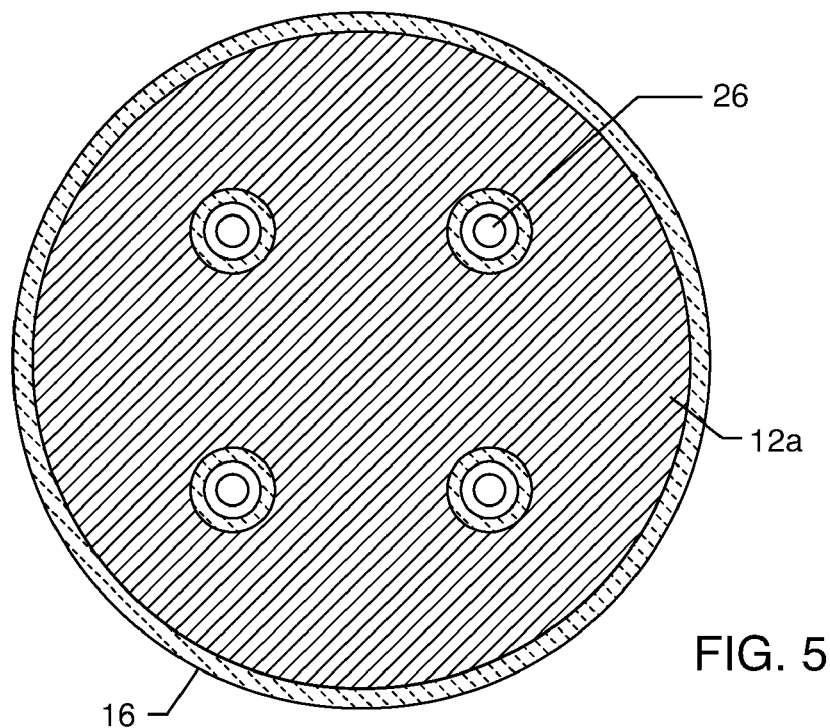
FIG. 5 is a cross-sectional view of the quadpolar feedthrough terminal assembly shown taken along line 5-5 in FIG. 2.
Figure 6:
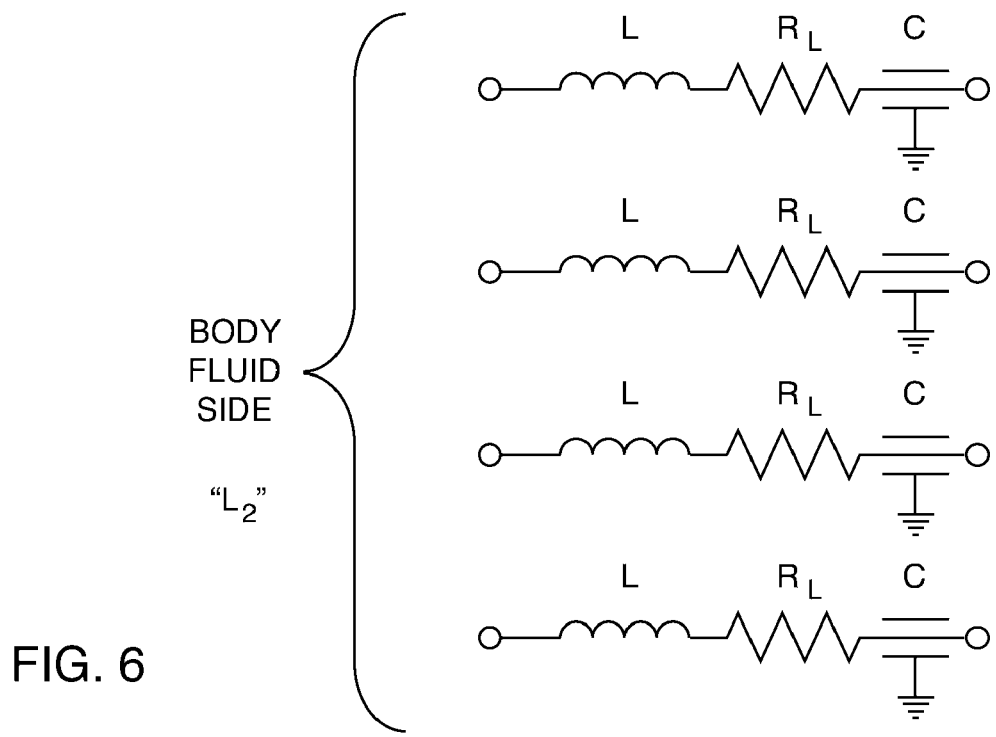
FIG. 6 is an electrical schematic diagram of the terminal of FIG. 1.

FIG. 5 depicts a cross-section from the novel insulator 16 of FIG. 2 illustrating a ferrous plate 12a, such as nickel, embedded in the insulator 16. The embedded plate(s) 12a provide a high degree of shielding against magnetic fields for the surface mounted inductor slab 32 and associated feedthrough capacitor 20.

Figure 12:
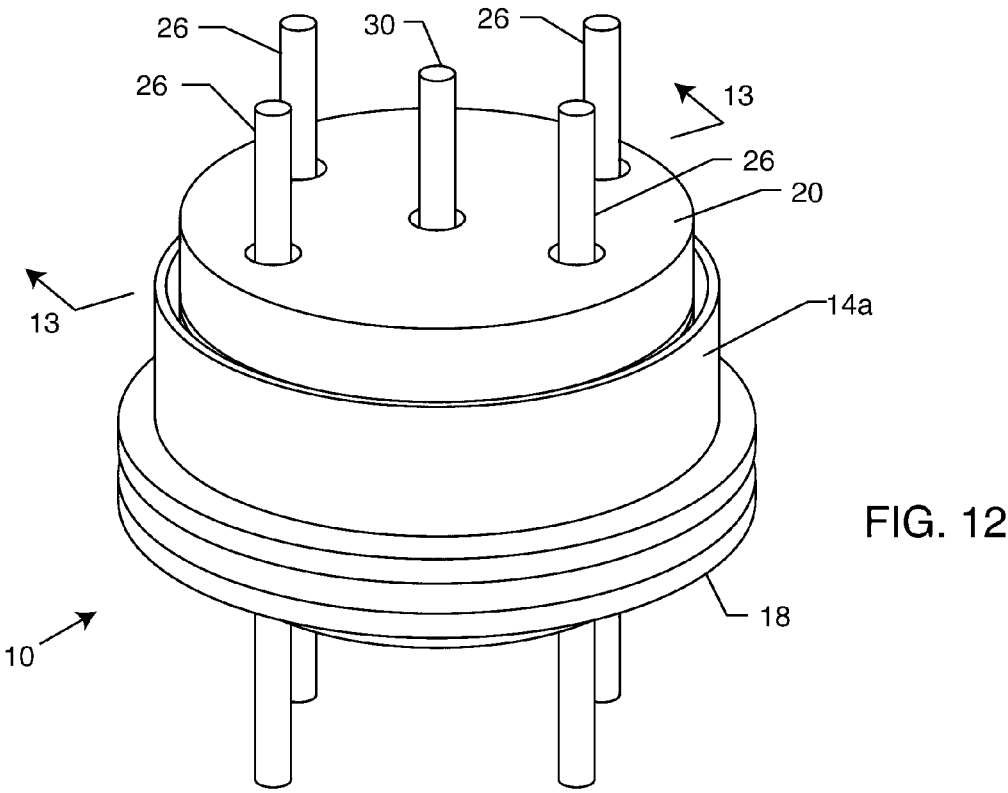
FIG. 12 is a perspective view of an internally grounded quadpolar feedthrough terminal assembly with an additional grounded pin embodying the present invention.
Figure 13:
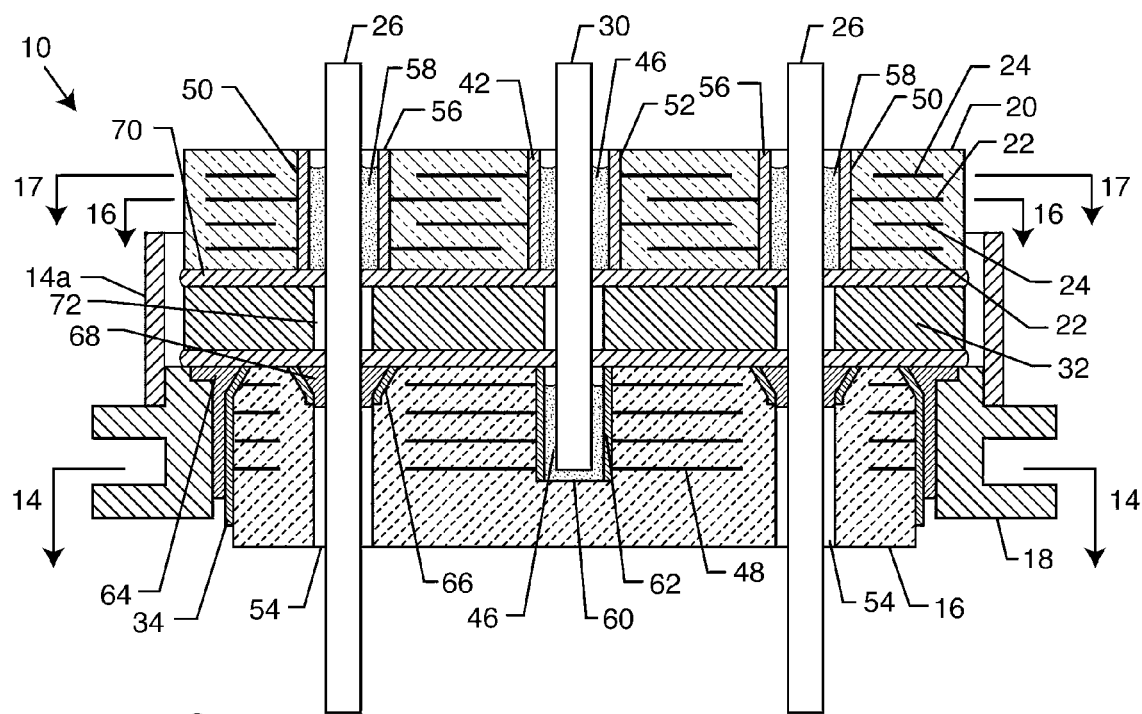
FIG. 13 is a cross-sectional view taken generally along line 13-13 of FIG. 12.
Figure 19:
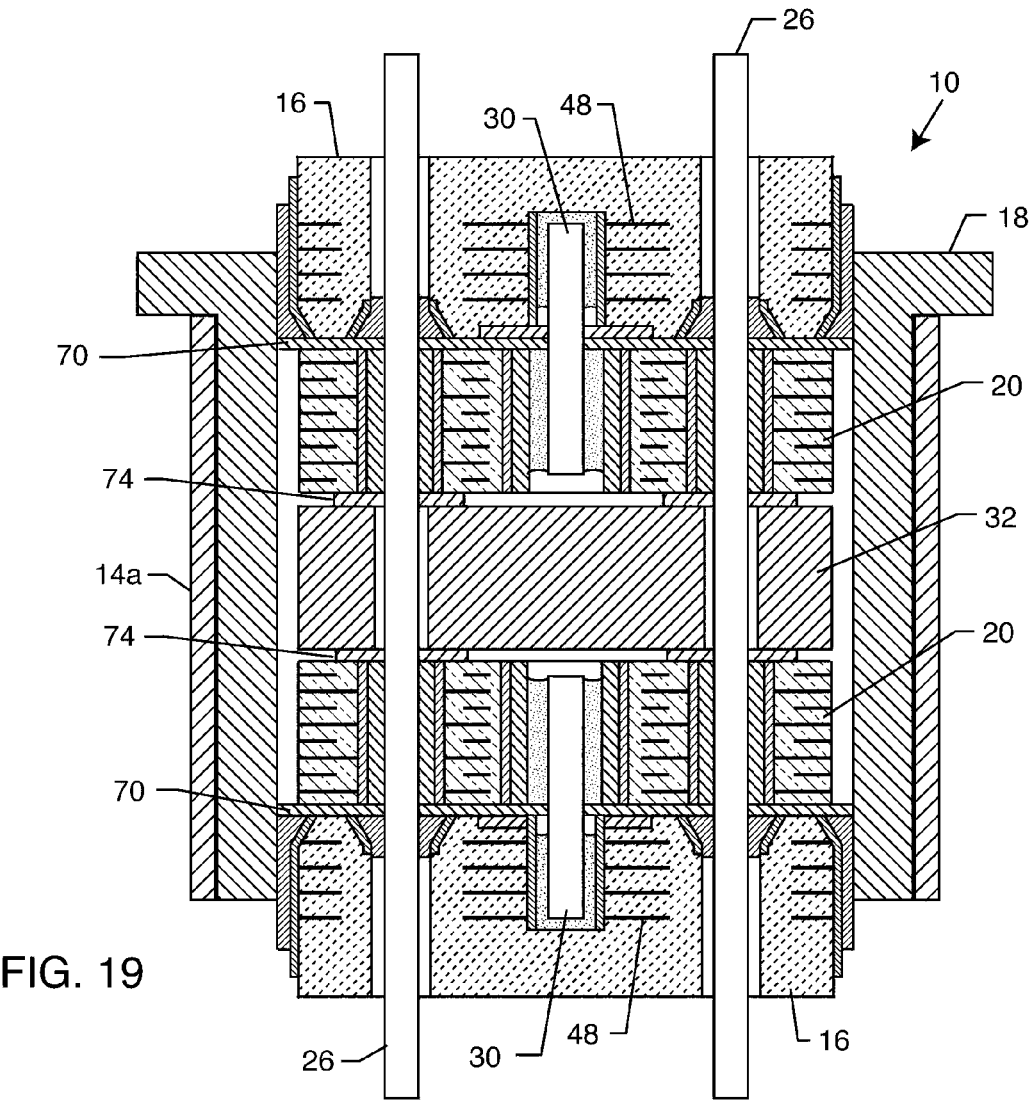
FIG. 19 is a cross-sectional view of a soldered-in quadpolar internally grounded "PI" filter feedthrough terminal assembly embodying aspects of the present invention.

Magnetic shielding provided by the interior magnetic shield 12 and/or the exterior magnetic shield 14 functions as intended regardless of whether said shield is grounded or not. The feedthrough capacitor 20 may be externally grounded, i.e., by means of an electrical connection between the second set of electrode plates 24, the outer diameter metallization 28 of the feedthrough capacitor 20 and the ferrule 18, housing or other ground plane. The feedthrough capacitor 20 may also be internally grounded by means of a grounded pin 30, i.e., a short pin that extends through the feedthrough capacitor 20 in conductive relation with the second set of electrode plates 24 and at least part way through the insulator 16 in conductive relation with embedded ground plates 48, as shown in FIGS. 12, 13 and 19.

A feedthrough terminal assembly 10 of the present invention may include one or more lossy ferrite inductor(s) 32 with both resistive and inductive properties, which is installed in proximity or adjacent to the feedthrough terminal assembly 10 of an active implantable medical device. The lossy ferrite inductor(s) 32 can be combined with one or more feedthrough capacitor(s) 20, which is mounted to the feedthrough terminal assembly 10. At least one terminal pin or lead wire 26 extends through the lossy ferrite inductor 32 in non-conductive relation. As described above, the lead wire 26 extends through the capacitor 20 in conductive relation with the first set of electrode plates 22. An outer ferrule 18, housing or ground plane is mounted adjacent to the capacitor 20 in conductive relation with the second set of electrode plates 24. The lossy ferrite inductor 32 works to absorb EMI energy (convert to heat) and increase the impedance of the lead wire 26. The feedthrough capacitor 20, which is well known in the art, reduces the impedance to ground thereby shunting or bypassing high frequency electromagnetic signals. The advantages of a lossy ferrite inductor 32 are described in copending U.S. patent application Ser. No. 11/097,999, filed Mar. 31, 2005, and U.S. Provisional Application No. 60/724,479, filed Oct. 6, 2005.

In the description of the drawings which follows, functionally equivalent components among the various embodiments will be designated by the same reference number.

Figure 7:
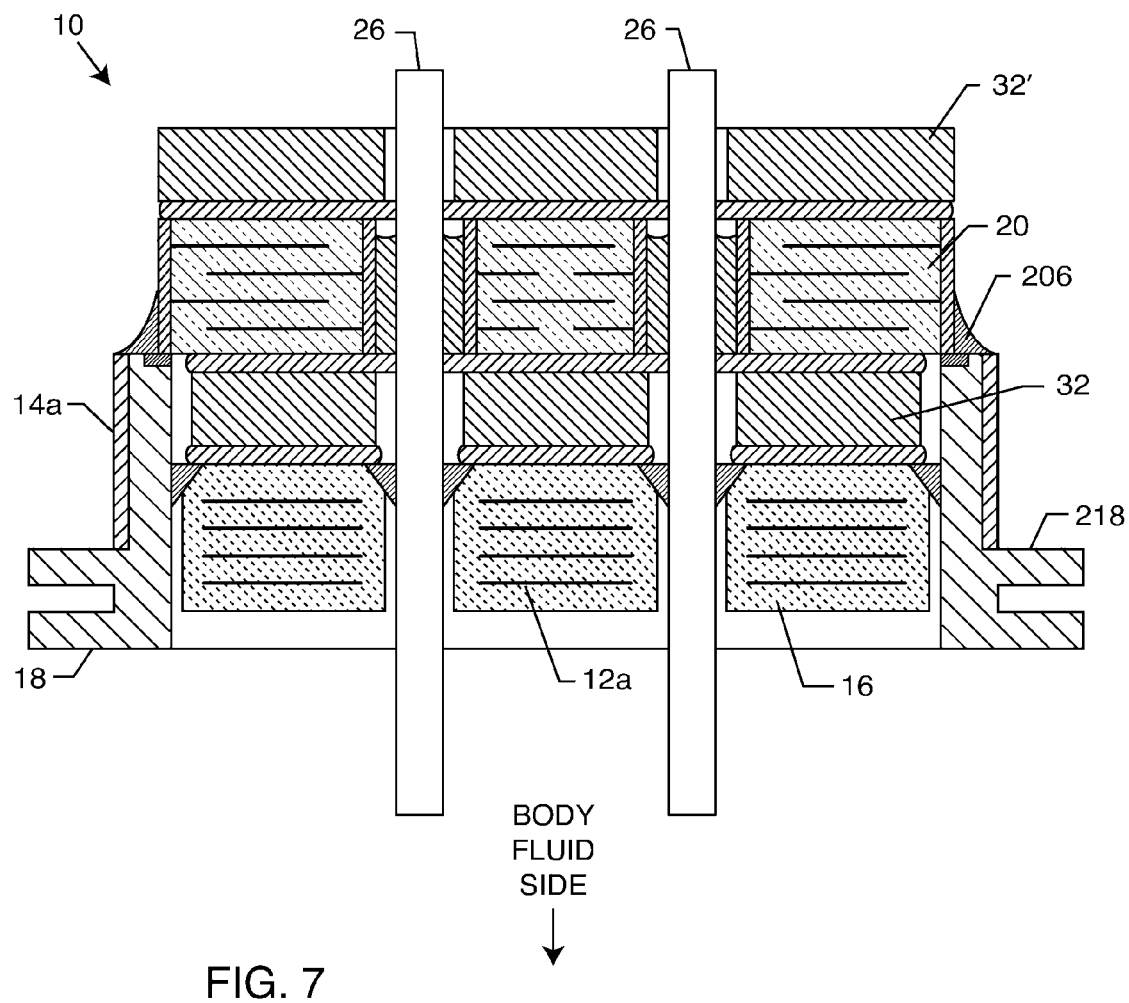
FIG. 7 is a sectional view similar to FIG. 2, of a "T" filtered feedthrough terminal wherein attachment material is shown connected to the capacitor outside diameter and to the ferrule and incorporating magnetic shield elements of the present invention.

FIG. 7 is a cross-sectional drawing illustrating an alternate configuration for a "T" filter feedthrough terminal assembly 10 embodying the internal magnetic shield 12 (embedded conductive plates 12a) and external magnetic shield 14 (conductive sleeve 14a) of the present invention. This configuration is highly efficient in that the lossy ferrite inductor 32 is oriented toward the body fluid side of the feedthrough terminal assembly 10. Lossy ferrite inductor 32' points toward the electronics of the AIMD thereby tending to stabilize the device's input impedance. This configuration is a very high performance EMI filter that will offer broad attenuation throughout the frequency range from 1 MHz to 100 MHz and above. EMI filters using only a capacitance circuit device, generally are only effective from 100 MHz to about 3 GHz. The configuration as shown in FIG. 7, has all the benefits of a feedthrough capacitor 20 with magnetic shields 12, 14, but with the added benefits of inductances and high frequency dissipative losses placed on both sides of the feedthrough capacitor 20. The performance of this configuration is not quite as high as the performance of other configurations, however, it is outstanding compared to all prior art devices incorporating only a feedthrough capacitor 20. Referring once again to FIG. 7, one will note that the lossy ferrite inductor 32 is shielded by the surrounding ferro-magnetic material 14a and the embedded plate 12a. Said lossy ferrite inductor can be further shielded by the use of base metal electrode plates 22, 24 in capacitor 20. These would be typically nickel electrodes. Using a cardiac pacemaker as an example, this device would be integral to the housing of the cardiac pacemaker. When the patient was exposed to a medical procedure such as MRI, the lossy ferrite inductor slab 32 would be protected or shielded from the main static magnetic field of the MRI. For example, the MRI might be 3 Teslas which produces a very powerful magnetizing force. In this case, the unshielded lossy ferrite inductor 32' would be mostly saturated. That is, its magnetic dipoles would line up with the static field of the MRI. On the other hand, lossy ferrite inductor 32, which is oriented towards the body fluid, would be protected from such saturation by the surrounding magnetic shielding materials as previously described. Accordingly, the "T" filter illustrated in FIG. 7 would continue to perform quite well in the presence of the main static field of the MRI. This is important in order to protect the interior electronics of the active implantable medical device from the MRI pulsed RF field. In the case of a 3 Tesla system, this pulsed RF field would operate at 128 MHz. Even though inductor 32' was mostly saturated, the remaining lossy ferrite slab inductor 32 with its associated feedthrough capacitor would still provide a very high degree of filter performance. In this case, when lossy ferrite slab inductor 32' is saturated, the filter would operate more like an "L" section filter.

FIG. 8 illustrates another alternate configuration for a feedthrough terminal assembly 10 embodying the internal magnetic shield 12 (embedded conductive plates 12a) and external magnetic shield 14 (conductive sleeve 14a) of the present invention. In this case, a first capacitor 20 is oriented toward the body fluid side. There are two lossy ferrite inductors 32, 32' sandwiched between the first capacitor 20 and a second capacitor 20' as shown. Inductor 32' is towards the AIMD electronic circuits. The first and second feedthrough capacitors 20, 20' both have external metallization 34, 34' in order to conduct their respective ground electrode plates 24, 24' in parallel. The conductive fill medium 36 that connects the ground plates 24, 24' of the two capacitors 20, 20' makes contact to this metallization 34, 34'. Conductive fill medium 36 makes contact to gold braze area 38 to provide a reliable oxide-free electrical connection to the ferrule 18. The ferrule 18 is connected to the overall housing of the AIMD which acts as an electromagnetic shield. In this way the ground electrode plates 24, 24' of both the lower and upper capacitors 20, 20' become a part of the continuous overall electromagnetic shield of the active implantable medical device. This configuration is particularly effective in that it has a very high attenuation slope rate. However, it would be preferred in an MRI application to have the inductance point towards the body fluid side. The reason for this is that capacitor 20 tends to lower the input impedance of the AIMD. This causes a corresponding increase in MRI currents in the lead wires 26 on the body fluid side. Accordingly, it would be preferable to have lossy ferrite inductor 32 swapped in place of capacitor 20 so that higher input impedance could be presented to the implanted lead wires 26. The ferrule 18 of the feedthrough terminal assembly 10 has been extended upward so as to provide an annular space that surrounds the feedthrough capacitors 20 and 20'. The conductive material 36 is placed to make an electrical contact to both of the lower and upper capacitor 20, 20' outside diameter ground termination areas 34, 34'. Also shown in FIG. 8 is an exterior magnetic shield 14 which comprises a cap 14b is disposed over the feedthrough capacitor 20 and 20' and the portion of the ferrule 18 that has been extended upward. This cap 14b provides magnetic shielding similar to the interior magnetic shield 12 and conductive plates 12a described above. Referring to FIG. 9, the exterior magnetic shield 14 in the form of the conductive cap 14b is shown separate from the feedthrough terminal assembly 10. Referring again to FIG. 8, the conductive cap 14b makes contact to gold braze area 40 to provide a reliable oxide free electrical connection to the ferrule 18. For magnetic shielding, it is actually not required that the shield and cap assembly 14 and 14b make solid electrical contact to ferrule 18. In fact, attachment to material 40 could be a nonconductive epoxy to simply seat the magnetic shield in place. Unlike electric or electromagnetic shields for high frequency, low frequency or static magnetic shields do not have to be continuous and well grounded. Referring once again to FIG. 8, one can see that lossy ferrite inductors 32 and 32' are now both shielded, for example, from the main static field of an MRI system. In this case, this would be a very robust EMI filter while operating in the presence of the MRI RF pulsed signal. The reason for this is that the feedthrough capacitors 20 and 20' are basically immune to the static field of the MRI. In other words, no magnetic shielding is really required for the feedthrough capacitors. However, the lossy ferrite inductors 32 and 32' operate through the presence of magnetic dipoles which present a resistive and inductive loss. They do this by opposing changes in current in the lead wires by interacting with the magnetic fields associated with said currents. Accordingly, it is a major improvement to prevent the saturation of these magnetic lossy elements 32 and 32' during the MRI procedure. Accordingly, "LL" circuit performance will be achieved providing a very high degree of attenuation for the MRI pulsed RF field. In addition, when the patient is not undergoing a medical procedure such as MRI, the patient could be exposed to other environmental emitters, such as cellular telephones, microwave ovens and the like. In this case, a very high degree of filtering would be provided for the patient due to the effectivity of the "LL" filter circuit configuration.

It should also be noted that it is not necessary to use all of the magnetic shielding elements at the same time as disclosed herein. For example, referring once again to FIG. 8, it may not be necessary to both provide the magnetic shield and its associated cap 14 and 14b along with magnetic shield plate set 12a. For example, one can eliminate magnetic shield set 12a. In this regard, there would only be a partial amount of magnetic shielding that was protecting the lossy ferrite slab 32 and 32' from saturating. However, as a cost tradeoff, sufficient filtering may still be provided. In other words, any of the individual elements as described in the present invention may be used either individually or in combination.

Figure 10:
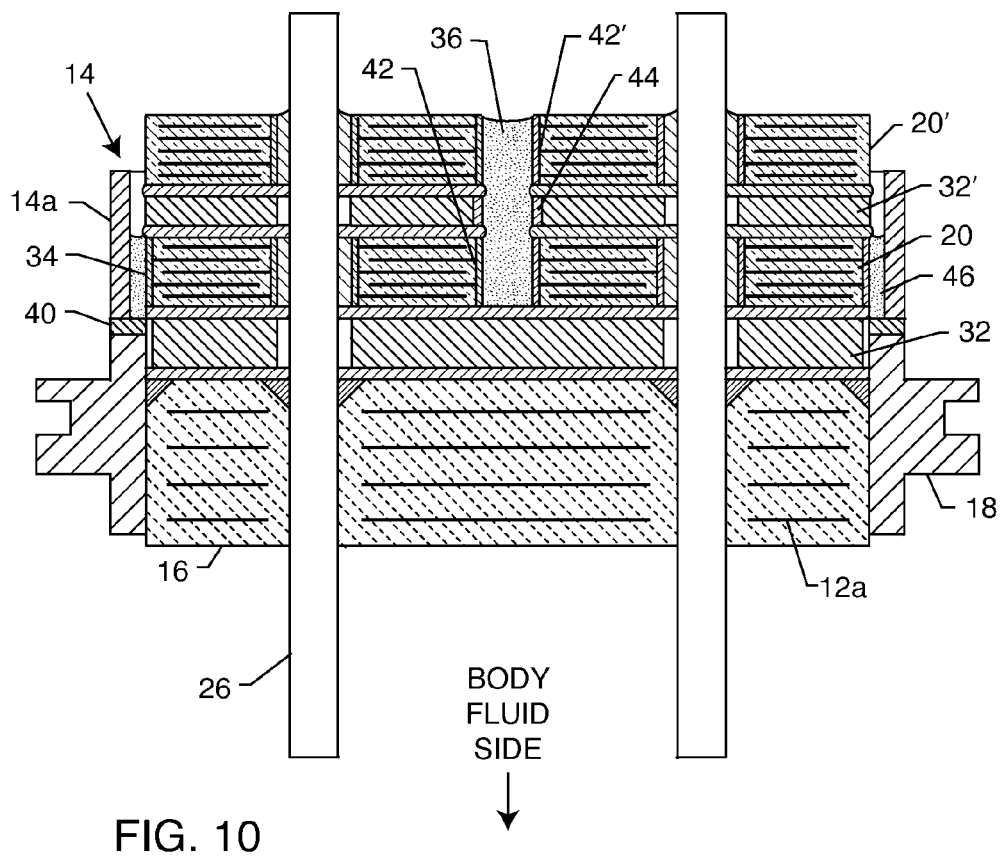
FIG. 10 is a cross-sectional view of a quadpolar "LL" filtered feedthrough terminal assembly incorporating magnetic shield elements of the present invention, wherein the first lossy ferrite inductor is oriented toward the body fluid side.

FIG. 10 illustrates the preferred embodiment of the configuration shown in FIG. 8 in that the lossy ferrite inductor 32 is now oriented toward the body fluid side lead wires 26. The lower capacitor 20 is a hybrid capacitor in that it has both external 34 and internal 42 metallization for connection to ground. The internal metallization 42 communicates with the ground through a conductive via hole. This via hole can contain a ground pin or be filled with a conductive material 36 such as a thermal setting conductive adhesive, a solder or the like. The important thing is that the ground hole of the hybrid capacitor 20 communicates with the ground plates and internal metallization 42' of the upper capacitor 20'. It is in this way that the ground electrodes of capacitor 20' are connected to a ground plane. In the case where the via hole is filled with a conductive medium 36, it is preferable to have additional insulation 44 on the inside diameter of the inductor slab 32' as shown. This additional insulation 44 can be of the group of any insulating material including non-conductive polymers, non-conductive epoxies, insulating sleeves, insulating tubing and the like. The upper and lower feedthrough capacitors 20, 20' both have internal metallization 42, 42' in order to conduct the respective ground electrode plates in parallel. The conductive fill medium 36 that connects these two capacitors 20, 20' together makes contact to this metallization 42, 42'. The outside diameter metallization 34 of the lower feedthrough capacitor 20 provides a reliable electrical connection to gold braze area 40 to complete the external grounding. The hybrid capacitor 20 is attached to an elevated ferrule 18 flange with conductive bonding material 46. Gold sputter or braze or equivalent material 40 has been added to the top of the ferrule flange 18 so that a reliable oxide free electrical connection can be formed from the outside diameter metallization 34 (ground metallization) of feedthrough capacitor 20 to the ferrule 18 (see U.S. Pat. Nos. 6,765,779 and 6,765,780). The feedthrough assembly 10 of FIG. 10 includes the optional interior magnetic shield 12 comprising one or more ferromagnetic shield plates 12a embedded in the insulator 16 as well as the exterior magnetic shield 14 comprising the conductive sleeve 14a. The conductive plates 12a are electrically isolated in the insulator 16. The conductive sleeve 14a makes contact to the braze area 40 to provide a reliable oxide-free electrical connection to the ferrule 18.

Figure 11:
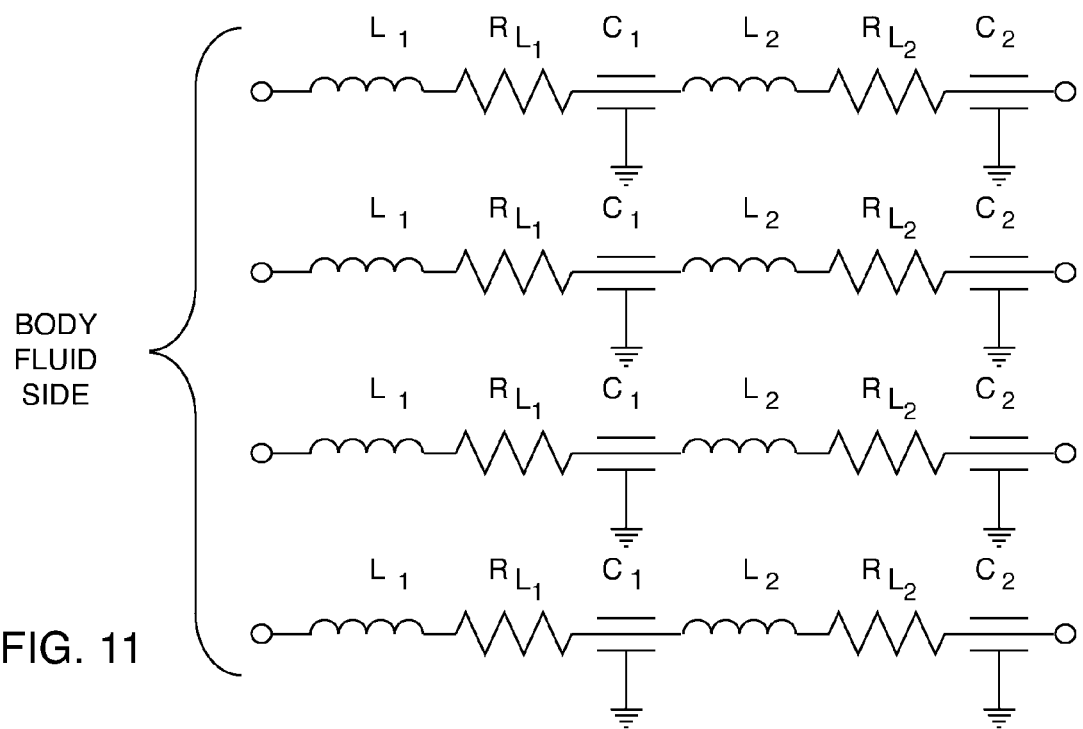
FIG. 11 is an electrical schematic diagram of the feedthrough terminal assembly illustrated in FIG. 10.

FIG. 11 is the schematic diagram of the feedthrough terminal assembly 10 described in FIG. 10. It is desirable to have lossy ferrite inductor(s) 32 oriented towards the body fluid side. This has the effect of raising the impedance of the implanted lead wire 26 and electrically isolating the lower and upper feedthrough capacitors 20, 20'. Also oriented toward the body fluid side is resistor $R_{L1}$. This is the high frequency lossy or ohmic electric characteristic of the lossy ferrite inductor 32. By orienting both the lossy ferrite inductor 32 and the resistor $R_{L1}$ towards the body fluid side, this serves to raise the impedance of the lead wires 26. As previously mentioned, this is highly desirable to reduce the amount of MRI current flowing in the lead wires 26. Less current means less heating and less tendency to cause venous or TIP/RING ablation (tissue damage). Such overheating has been noted in the reference literature and is highly undesirable.

Referring to FIGS. 12-18, the "L" filter feedthrough terminal assembly 10 comprises, generally, a plurality (in this case four) conductive lead wires 26 which extend through a conductive ferrule 18, in non-conductive relation, as will be more fully described herein. An insulator 16 (FIG. 13) supports each conductive lead wire 26 relative to the conductive ferrule 18 in electrically insulated relation. The insulator 16 is typically comprised of an alumina ceramic material, although it is not limited to such. However, the insulator 16 must be comprised of an electrically non-conductive material. The alumina insulator 16 includes at least one embedded monolithic ground plate 48 (see FIGS. 13 and 14), and preferably a plurality of ground plates 48 spaced apart from one another to form a set, whose purpose will be described more fully herein. In accordance with the present invention, the feedthrough terminal assembly 10 includes an external magnetic shield 14 comprising a conductive sleeve 14a. The internal magnetic shield 12 is omitted in favor of the ground plates 48 described previously. In the preferred embodiment, the embedded ground plates 48 will be both highly conductive and ferromagnetic. An ideal material for this is nickel. In this case, embedded nickel plates will provide magnetic shielding from the main static field of MRI and also provide and very low impedance connection to ground for the capacitor grounding pin 30.

Figure 16:
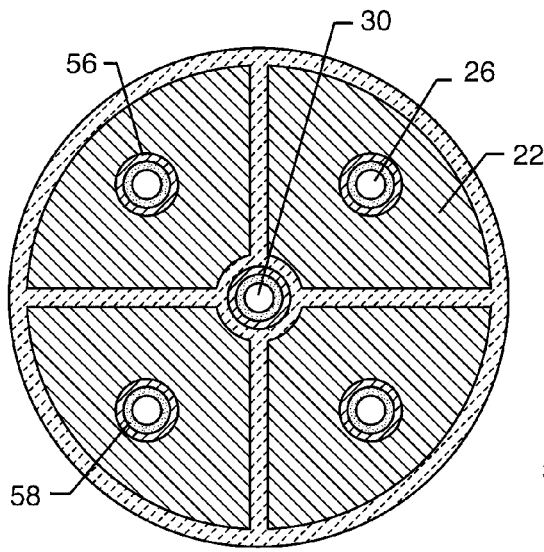
FIG. 16 is a cross-sectional view taken generally along line 16-16 of FIG. 13.
Figure 17:
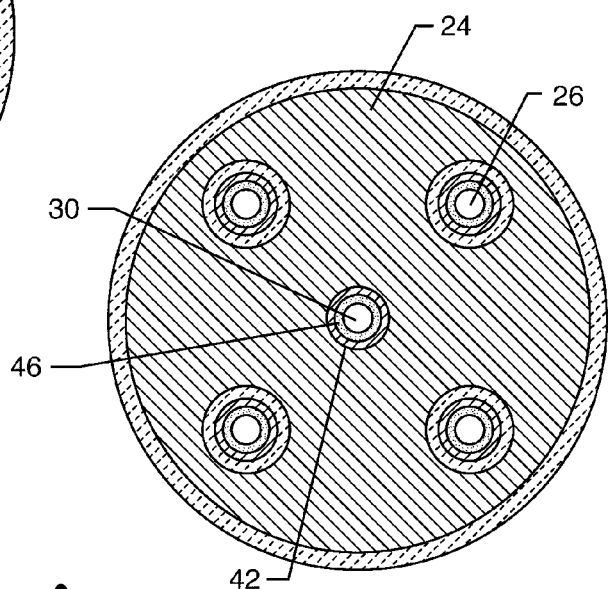
FIG. 17 is a cross-sectional view taken generally along line 17-17 of FIG. 13.

The feedthrough terminal assembly 10 further includes an internally grounded feedthrough capacitor 20 that has first and second sets of electrode plates 22, 24 (FIGS. 13, 16 and 17). Passageways 50 are provided through the feedthrough capacitor 20 through which the lead wires 26 extend in conductive relation with the first set of electrode plates 22. The feedthrough capacitor 20 further includes a second passageway 52 into which a conductive ground pin 30 extends in conductive relation to the second set of electrode plates 24.

In accordance with the present invention, the feedthrough terminal assembly 10 includes a monolithic, ceramic, internally grounded feedthrough capacitor 20 having two or more (in this instance five) passageways 50, 52 extending therethrough. Internally grounded electrodes are described by U.S. Pat. Nos. 5,905,627 and 6,529,103. Described herein is a novel method of providing a ground inside of the hermetic insulator for use in internally grounding the ground electrode plate set 24 of the capacitor 20. The outer four passageways 50 are configured to receive therethrough the respective conductive lead wires 26, and the internal diameter of the first passageways 50 are metallized (at 56) to form a conductive link between the first set of electrode plates 22 and the conductive lead wires 26. A conductive polyimide fill, solder, or the like 58 is placed within the first passageways 50 between the metallization 56 and the respective lead wire 26 to electrically link the lead wire 26 with the respective first set of electrode plates 22. As is well understood in the art, both sets of electrode plates 22, 24 are typically silk-screened onto ceramic plates, forming the feedthrough capacitor 20. These plates 22, 24 are surrounded by an insulative ceramic material 20a that, for purposes of the present invention, need not be metallized on its exterior surfaces, as will be more fully discussed herein.

Similarly, the inner diameter of the central or second passageway 52 through the feedthrough capacitor 20 is also metallized (at 42) to conductively connect the second set of electrode plates 24, also referred to as the ground plates of the feedthrough capacitor 20. As discussed above, the second passageway 52 is configured to receive therethrough the conductive ground pin 30. Again, a conductive polyimide, solder or other conductive fill 46 is placed within the second passageway 52 between the ground pin 30 and the metallization 42 to conductively couple the ground pin 30 to the second set of electrode plates 24.

In typical applications in the prior art, the second set of ground electrodes 24 extend to the outer periphery of the capacitor 20. The outer surface of the capacitor 20 is then metallized by metallization firing or plating operations, or otherwise providing external conductive connections between capacitor 20 and a ground, typically the conductive ferrule 84. However, in addition to requiring extra manufacturing steps, forming such conductive connections places a great deal of stress on the capacitor 20 during the manufacturing process and also presents drawbacks of the joining of materials which are not perfectly matched in thermal coefficient of expansion.

The present invention, as described herein, eliminates the need for such external conductive connections between the capacitor 20 and the ferrule 18, or other ground. Typically, the conductive ferrule 18 is conductively mounted to a conductive substrate that may comprise, for example, the housing for an active implantable medical device. The ground pin 30, which is electrically and conductively coupled to the second set of electrode plates 24, as discussed above, extends into the insulator 16 so as to be conductively coupled with the one or more ground plates 48 of the insulator 16. More particularly, as illustrated in FIG. 13, the insulator 16 includes a passageway 60 adapted to receive the ground pin 30 therethrough. The ground plates 48 extend to the surface of this passageway 60, which is metallized (at 62) to conductively couple the ground plate 48 to one another. A conductive polyimide, solder, or other conductive fill 46 is placed within the passageway 60 to conductively couple the ground pin 30 to the ground plates 48.

Figure 14:
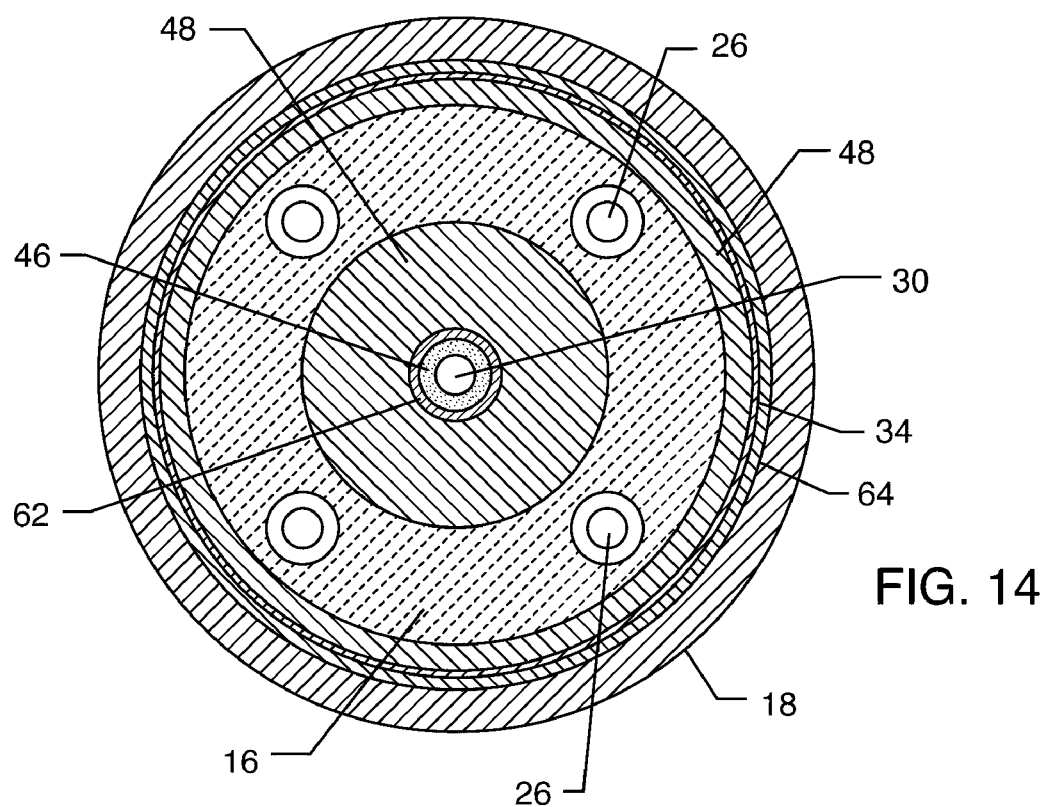
FIG. 14 is a cross-sectional view taken generally along line 14-14 of FIG. 13.
Figure 15:
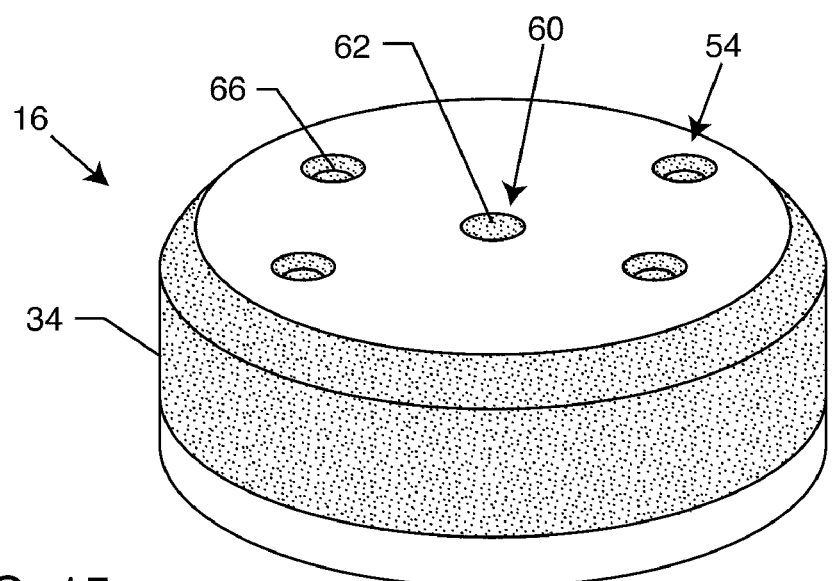
FIG. 15 is a side perspective view of the insulator of FIG. 12.

The ground plates 48, as shown in FIGS. 13 and 14, extend to the outer peripheral surface of the insulator 16, which includes a metallization 34 (FIG. 15). This metallization 34 can be formed by any means, including electroplating, thick film deposition, sputtering, or the like. The metallization 34 is conductively coupled to the ferrule 18, such as through the use of a conductive pre-form, solder, weld, braze or the like 64. Thus, the second set of electrode plates 24 of the feedthrough capacitor 20 are conductively coupled to the internal ground pin 30, which in turn is conductively coupled to the one or more ground plates 48 of the insulator 16, which are conductively coupled to the ferrule 18. As previously mentioned, the embedded ground electrode plates 48 can also be of ferrous material such as nickel so that both grounding of the internal ground pin 30, as well as, magnetic shielding of the lossy ferrite inductor 32 can be accomplished. Further shielding of the lossy ferrite inductor 32 is accomplished by the external magnetic cylindrical shield 14a.

Passageways 54 are also formed through the insulator 16, in general alignment with the capacitor passageways 50, for passage of the lead wires 26 therethrough. Due to the non-conductive nature of the material comprising insulator 16, the lead wires 26 could pass through in a frictional fit manner. However, in a particularly preferred embodiment, an upper beveled portion of the passageway 54 is metallized 66 (see FIG. 15) such that a metal braze pre-form, such as gold or the like, 68 can securely and hermetically connect the lead wire 26 to the insulator 16. However, the metallization 66 does not come into contact with the one or more ground plates 48. Thus, the lead wires 26 are electrically isolated from the ground plates 48 and the ferrule 18.

Figure 18:
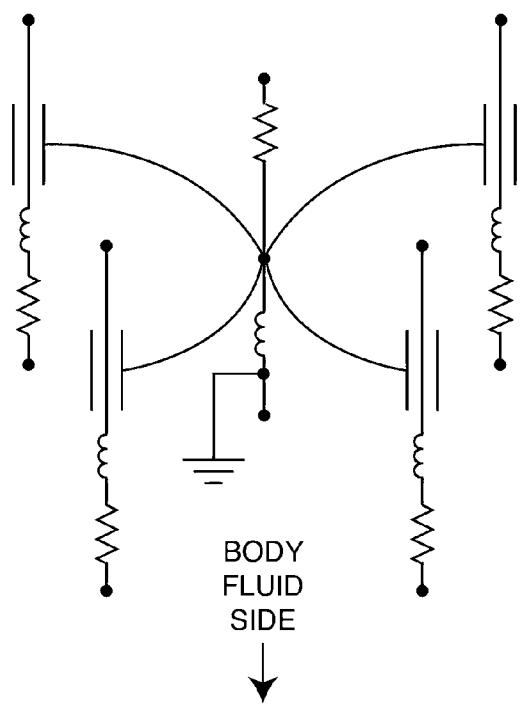
FIG. 18 is an electrical schematic representation illustrating the filtering characteristics of the assembly of FIG. 12.

With continuing reference to FIG. 13, the capacitor 20 and insulator 16 are typically disposed relatively adjacent to one another and separated by a lossy ferrite inductor 32, as illustrated in FIG. 13. An insulative washer 70 is disposed between the inductor 32 and the capacitor 20 to provide a physical separation between them. Passageways 72 are formed in the inductor 32, as necessary, such that the lead wires 26 and ground pin 30 pass therethrough. It will be understood by those skilled in the art that the assembly 10 may incorporate one or more ferrite inductors 32 in various EMI filter circuit configurations as needed or desired. The electrical schematic for the configuration of the assembly 10 in FIGS. 12 and 13 is illustrated in FIG. 18.

As shown in FIGS. 12 and 13, the ground pin 30 may extend well above the capacitor 20 surface if needed for convenient connection of an internal circuit or substrate to the ground (ferrule 18 or active implantable medical device housing). However, the ground pin 30 does not have to penetrate all the way through the insulator 16.

Figure 20:
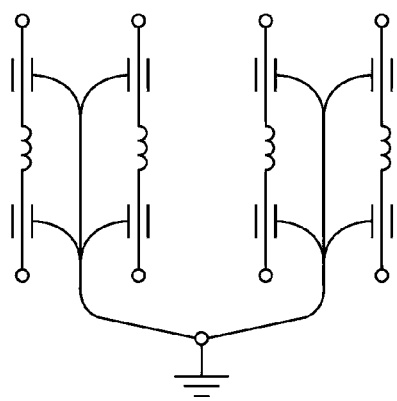
FIG. 20 is an electrical schematic representation for the assembly of FIG. 19.

With reference now to FIGS. 19 and 20, another alternative configuration for a feedthrough terminal assembly 10 is illustrated. Here, two ground pins 30 are utilized with their respective pair of feedthrough capacitors 20 and insulators 16 containing ground plates 48, as illustrated and described above. The pair of feedthrough capacitors 20 and insulators 16 are disposed on opposite sides of an intermediate inductor 32. The inductor 32, capacitors 20, and insulators 16 are separated by insulative washers 70 and 74. The electrical schematic for the assembly 10 shown in FIG. 19 is illustrated in FIG. 20. As with the embodiment shown in FIGS. 12 and 13, the feedthrough terminal assembly 10 possesses an exterior magnetic shield 14 comprising a ferro-magnetic sleeve 14a surrounding the ferrule 18. The interior magnetic shield 12 is omitted in favor of the preferably nickel ground plates 48.

Figure 21:
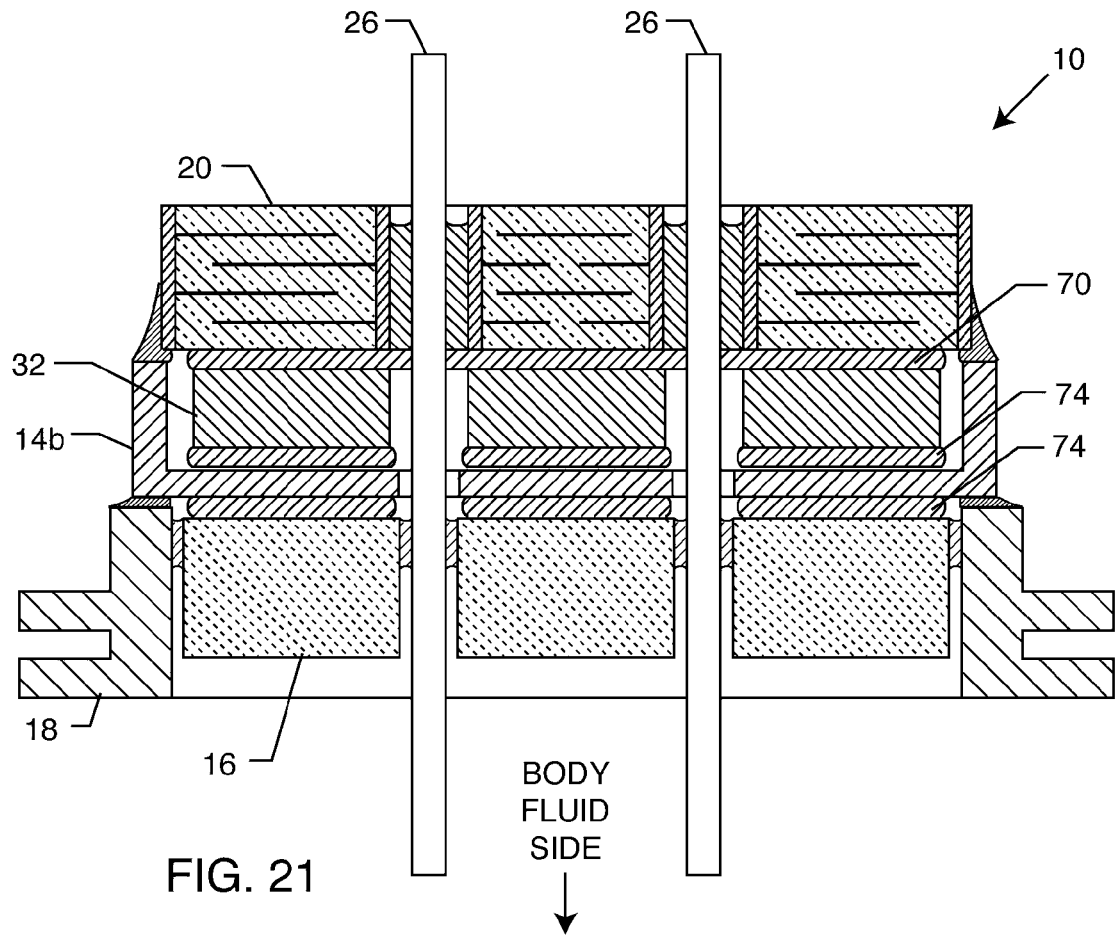
FIG. 21 is a sectional view of an "L" filtered feedthrough terminal assembly incorporating magnetic shield elements of the present invention.
Figure 22:
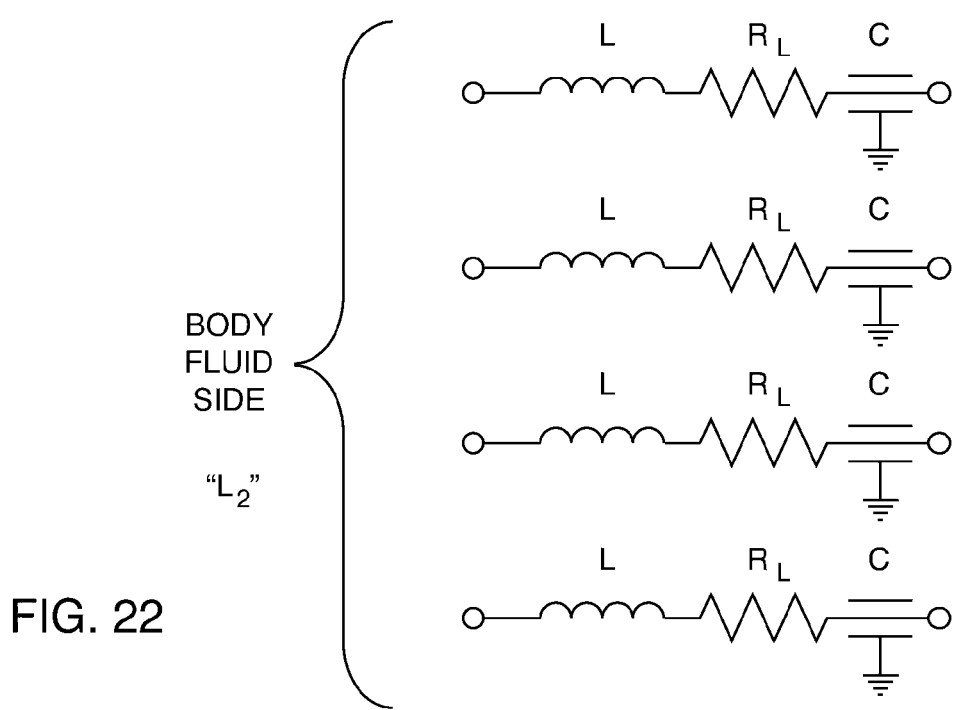
FIG. 22 is an electrical schematic diagram of the terminal of FIG. 21.
Figure 23:
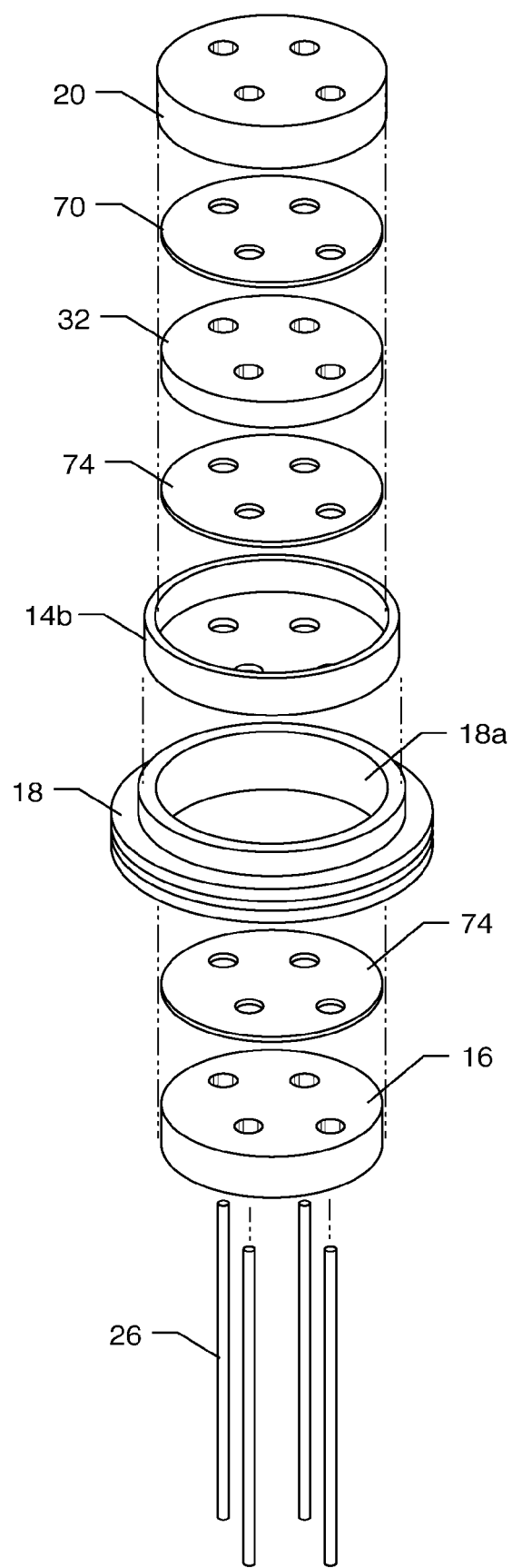
FIG. 23 is an exploded perspective view of the feedthrough terminal assembly of FIG. 21.

With reference to FIGS. 21, 22 and 23, an "L" filter feedthrough terminal assembly 10 is illustrated. This is a quadpolar device as illustrated in the schematic diagram of FIG. 22. As described above, placing the lossy ferrite inductor 32 toward the body fluid side of the assembly 10 acts to increase the impedance on the lead wires 26. By positioning capacitor 20 on the other side of the lossy ferrite inductor 32, its relatively low impedance is then positioned to protect the internal electronics of the device but not unduly lower the impedance of the implanted lead wires 26. This device includes an exterior magnetic shield 14 in the form of a conductive cap 14b which is inverted and placed around the lossy ferrite inductor 32. As with the other magnetic shields described above this cap 14b protects the internal components of an active implantable medical device from incident magnetic fields. FIG. 23 is an exploded perspective view of a feedthrough terminal assembly 10 of the present invention demonstrating the relationship of the feedthrough capacitor 20, the lossy ferrite inductor 32, the conductive cap 14b, the ferrule 18 including aperture 18a, the insulator 16, the lead wires 26, and the various insulative washers 70, 74. The inverted cap arrangement 14b, as illustrated in FIG. 21, is particularly desirable in the case where the overall housing of the active implantable medical device includes magnetic shielding. Such magnetic shields have been described in U.S. Pat. Nos. 5,217,010, 6,765,144, 6,815,609 and the like. Having a continuous magnetic shield protects the components that are internal to the housing of the active implantable medical device. Referring back to FIG. 21, the presence of the inverted cap 14b provides additional shielding in the area where the lead wires 26 pass through the hermetic insulator 16. In this case, embedded electromagnetic shield plates 12a inside of the hermetic insulator 16 are not required.

Although several different embodiments of the present invention have been illustrated and described in detail, various modifications may be made without departing from the spirit and scope of the invention. Accordingly, the invention is not to be limited, except as by the appended claims.

What is claimed is:

1. A feedthrough terminal assembly having magnetic shielding characteristics, comprising:
   a conductive support defining a central aperture;
   an insulator disposed over the central aperture of the conductive support, having a conductive plate embedded in the insulator forming an interior magnetic shield across substantially the entire central aperture of the conductive support;
   a feedthrough capacitor disposed on an axial side of the insulator, the feedthrough capacitor having first and second sets of electrode plates, the second set of electrode plates being conductively coupled to the conductive support or a ground plane; and
   a lead wire extending through the insulator and the feedthrough capacitor in non-conductive relation with the conductive support and conductively coupled to the first set of electrode plates.

2. The assembly of claim 1, wherein the conductive support comprises a ferrule or a housing.

3. The assembly of claim 1, wherein the interior magnetic shield comprises a set of conductive plates embedded in the insulator.

4. The assembly of claim 3, wherein the conductive plates are comprised of materials containing magnetic dipoles, such as nickel, ferrous materials, and nano-powders.

5. The assembly of claim 2, including an exterior magnetic shield peripherally surrounding at least a portion of the ferrule and/or feedthrough capacitor.

6. The assembly of claim 5, wherein the exterior magnetic shield includes a cap disposed over the feedthrough capacitor opposite the insulator.

7. The assembly of claim 5, wherein the exterior magnetic shield is comprised of a ferro-magnetic material, such as nickel or nickel alloy.

8. The assembly of claim 5, further including a lossy ferrite inductor disposed between the capacitor and the insulator through which the lead wire extends in non-conductive relation.

9. The assembly of claim 8, wherein the feedthrough capacitor comprises first and second feedthrough capacitors associated with the lossy ferrite inductor.

10. The assembly of claim 9, wherein the first and second feedthrough capacitors are disposed adjacent to opposite surfaces of the lossy ferrite inductor.

11. The assembly of claim 9, wherein the first and second feedthrough capacitors each include a first set of electrode plates conductively coupled to the lead wire, and a second set of electrode plates conductively coupled to the housing, ferrule, or ground plane.

12. The assembly of claim 1, wherein the feedthrough terminal assembly is suitable for use in an active implantable medical device such as a cardiac pacemaker, an implantable defibrillator, a congestive heart failure device, a hearing implant, a cochlear implant, a neurostimulator, a drug pump, a ventricular assist device, an insulin pump, a spinal cord stimulator, an implantable sensing system, a deep brain stimulator, an artificial heart, an incontinence device, a vagus nerve stimulator, a bone growth stimulator, a bion, a gastric pacemaker, or a prosthetic device.

13. A feedthrough terminal assembly having magnetic shielding characteristics, comprising:
a conductive support defining a central aperture;
an insulator disposed over the central aperture of the conductive support;
an magnetic shield disposed across substantially the entire central aperture of the conductive support;
a feedthrough capacitor disposed on an axial side of the insulator, the feedthrough capacitor having first and second sets of electrode plates, the second set of electrode plates being conductively coupled to the conductive support or a ground plane; and
a lead wire extending through the insulator and the feedthrough capacitor in non-conductive relation with the conductive support and conductively coupled to the first set of electrode plates.

14. The assembly of claim 13, wherein the conductive support comprises a ferrule or a housing.

15. The assembly of claim 13, wherein the magnetic shield comprises a conductive plate disposed between the insulator and the feedthrough capacitor, through which the lead wire passes in non-conductive relation.

16. The assembly of claim 15, wherein the magnetic shield includes an exterior portion at its periphery conductively coupling the second set of electrode plates to the conductive support.

17. The assembly of claim 13, further including a lossy ferrite inductor disposed between the capacitor and the insulator through which the lead wire extends in non-conductive relation.

18. The assembly of claim 17, wherein the feedthrough capacitor comprises first and second feedthrough capacitors associated with the lossy ferrite inductor.

19. The assembly of claim 18, wherein the first and second feedthrough capacitors are disposed adjacent to opposite surfaces of the lossy ferrite inductor.

20. The assembly of claim 18, wherein the first and second capacitors each include a first set of electrode plates conductively coupled to the lead wire, and a second set of electrode plates conductively coupled to the conductive support or the ground plane.

21. The assembly of claim 13, wherein the magnetic shield comprises a conductive plate embedded in the insulator and forming an interior magnetic shield.

22. The assembly of claim 21, wherein the interior magnetic shield comprises a set of conductive plates embedded in the insulator.

23. The assembly of claim 22, wherein the conductive plates are comprised of materials containing magnetic dipoles, such as nickel, ferrous materials, and nano-powders.

24. The assembly of claim 14, including an exterior magnetic shield peripherally surrounding at least a portion of the ferrule and/or feedthrough capacitor.

25. The assembly of claim 24, wherein the exterior magnetic shield includes a cap disposed over the feedthrough capacitor opposite the insulator.

26. The assembly of claim 24, wherein the exterior magnetic shield is comprised of a ferro-magnetic material, such as nickel or nickel alloy.

27. The assembly of claim 24, wherein the exterior magnetic shield conductively couples the second set of electrode plates to the conductive support.

28. The assembly of claim 13, wherein the feedthrough terminal assembly is suitable for use in an active implantable medical device such as a cardiac pacemaker, an implantable defibrillator, a congestive heart failure device, a hearing implant, a cochlear implant, a neurostimulator, a drug pump, a ventricular assist device, an insulin pump, a spinal cord stimulator, an implantable sensing system, a deep brain stimulator, an artificial heart, an incontinence device, a vagus nerve stimulator, a bone growth stimulator, a bion, a gastric pacemaker, or a prosthetic device.

29. A feedthrough terminal assembly having magnetic shielding characteristics, comprising:
a conductive support defining a central aperture;
an insulator disposed over the central aperture of the conductive support;
a magnetic shield cup disposed on an axial side of the insulator wherein the magnetic shield covers substantially the entire central aperture of the conductive support;
a feedthrough capacitor disposed internally in the magnetic shield cup on the same axial side of the insulator, the feedthrough capacitor having first and second sets of electrode plates, the second set of electrode plates being conductively coupled to the conductive support or a ground plane; and
a lead wire extending through the insulator, the feedthrough capacitor and the magnetic shield cup in non-conductive relation with the conductive support and conductively coupled to the first set of electrode plates.

30. The assembly of claim 29, wherein the conductive support comprises a ferrule or a housing.

31. The assembly of claim 29, further comprising a conductive plate embedded in the insulator forming an interior magnetic shield across substantially the entire central aperture of the conductive support.

32. The assembly of claim 31, wherein the interior magnetic shield comprises a set of conductive plates embedded in the insulator.

33. The assembly of claim 32, wherein the conductive plates are comprised of materials containing magnetic dipoles, such as nickel, ferrous materials, and nano-powders.

34. The assembly of claim 29, wherein the magnetic shield cup is comprised of a ferro-magnetic material, such as nickel or nickel alloy.

35. The assembly of claim 29, further including a lossy ferrite inductor disposed between the capacitor and the insulator to which the lead wire extends in non-conductive relation.

36. The assembly of claim 35, wherein the feedthrough capacitor comprises first and second feedthrough capacitors associated with the lossy ferrite inductor.

37. The assembly of claim 36, wherein the first and second feedthrough capacitors are disposed adjacent to opposite surfaces of the lossy ferrite inductor.

38. The assembly of claim 36, wherein the first and second feedthrough capacitors each include a first set of electrode plates conductively coupled to the lead wire and a second set of electrode plates conductively coupled to the conductive support or the ground plane.

39. The assembly of claim 29, wherein the magnetic shield cup includes an exterior portion at its periphery conductively coupling the second set of electrode plates to the conductive support.

40. The assembly of claim 29, wherein the feedthrough terminal assembly is suitable for use in an active implantable medical device such as a cardiac pacemaker, an implantable defibrillator, a congestive heart failure device, a hearing implant, a cochlear implant, a neurostimulator, a drug pump, a ventricular assist device, an insulin pump, a spinal cord stimulator, an implantable sensing system, a deep brain stimulator, an artificial heart, an incontinence device, a vagus nerve stimulator, a bone growth stimulator, a bion, a gastric pacemaker, or a prosthetic device.

41. A feedthrough terminal assembly having magnetic shielding characteristics, comprising:
   a conductive support defining a central aperture;
   an insulator disposed over the central aperture of the conductive support having a conductive ground plate embedded in the insulator forming an interior magnetic shield across substantially the entire central aperture of the conductive support in conductive relation with the conductive support or a ground plane;
   a feedthrough capacitor disposed on an axial side of the insulator, the feedthrough capacitor having first and second sets of electrode plates;
   a lead wire extending through the insulator and the feedthrough capacitor in non-conductive relation with the conductive support and conductively coupled to the first set of electrode plates; and
   a conductive ground pin extending through the feedthrough capacitor in conductive relation with the second set of electrode plates and extending into the insulator in conductive relation with the conductive ground plate.

42. The assembly of claim 41, wherein the conductive support comprises a ferrule or a housing.

43. The assembly of claim 41, wherein the conductive ground plate comprises a set of conductive ground plates embedded in the insulator.

44. The assembly of claim 43, wherein the conductive ground plates are comprised of materials containing magnetic dipoles, such as nickel, ferrous materials, and nano-powders.

45. The assembly of claim 42, including an exterior magnetic shield peripherally sounding at least a portion of the ferrule and/or feedthrough capacitor.

46. The assembly of claim 45, wherein the exterior magnetic shield includes a cap disposed over the feedthrough capacitor opposite the insulator.

47. The assembly of claim 45, wherein the exterior magnetic shield is comprised of a ferro-magnetic material, such as nickel or nickel alloy.

48. The assembly of claim 45, further including a lossy ferrite inductor disposed between the capacitor and the insulator through which the lead wire and the conductive ground pin both extend in non-conductive relation.

49. The assembly of claim 48, wherein the feedthrough capacitor comprises first and second feedthrough capacitors associated with the lossy ferrite inductor.

50. The assembly of claim 49, wherein the first and second feedthrough capacitors are disposed adjacent to opposite surfaces of the lossy ferrite inductor.

51. The assembly of claim 49, wherein the first and second feedthrough capacitors each include a first set of electrode plates conductively coupled to the lead wire, and a second set of electrode plates conductively coupled to the conductive ground pin.

52. The assembly of claim 41, wherein the feedthrough terminal assembly is suitable for use in an active implantable medical device such as a cardiac pacemaker, an implantable defibrillator, a congestive heart failure device, a hearing implant, a cochlear implant, a neurostimulator, a drug pump, a ventricular assist device, an insulin pump, a spinal cord stimulator, an implantable sensing system, a deep brain stimulator, an artificial heart, an incontinence device, a vagus nerve stimulator, a bone growth stimulator, a bion, a gastric pacemaker, or a prosthetic device.

\* \* \* \* \*